United States Patent
Khetani et al.

(10) Patent No.: US 8,617,815 B2
(45) Date of Patent: Dec. 31, 2013

(54) MOLECULES WITH EFFECTS ON CELLULAR DEVELOPMENT AND FUNCTION

(75) Inventors: Salman R. Khetani, Cambridge, MA (US); Sangeeta N. Bhatia, Lexington, MA (US)

(73) Assignee: The Regents of the University of California, Oakland, CA (US)

( * ) Notice: Subject to any disclaimer, the term of this patent is extended or adjusted under 35 U.S.C. 154(b) by 1057 days.

(21) Appl. No.: 11/658,980

(22) PCT Filed: Aug. 4, 2005

(86) PCT No.: PCT/US2005/027604
§ 371 (c)(1),
(2), (4) Date: Jan. 29, 2007

(87) PCT Pub. No.: WO2006/015368
PCT Pub. Date: Feb. 9, 2006

(65) Prior Publication Data
US 2009/0202471 A1    Aug. 13, 2009

Related U.S. Application Data

(60) Provisional application No. 60/599,402, filed on Aug. 5, 2004.

(51) Int. Cl.
*C12Q 1/68*     (2006.01)
*C12N 5/07*     (2010.01)

(52) U.S. Cl.
USPC ............ 435/6.11; 435/6.1; 435/377; 435/347

(58) Field of Classification Search
None
See application file for complete search history.

(56) References Cited

U.S. PATENT DOCUMENTS

2001/0031462 A1    10/2001    Glynne et al.

OTHER PUBLICATIONS

Bhandari et al., Tissue Engineering, 7(3):345-357, 2001.
Bhadriraju et al., Drug Discovery Today, 7(11):612-620, 2002.
Gressner et al., Hepatology, pp. 571-581, 1996.
Muschen et al., Hepatology, 27(1):200-208, 1998.
Su et al., Proc. Nat. Acad. Sci., 99(17):11181-11186, 2002.
Waring et al., Toxicology and Applied Pharmacology, 175:28-42, 2001.
Bhatia S.N. et al. *FASEB Journal*, 13(14) pp. 1883-1900, Nov. 1, 1999.
Supplementary European Search Report for EP 05 80 4091, dated Nov. 20, 2008, 2 pgs.
Khetani S.R. et al. *Proceedings of the Second Joint EMBS-BMES Conference*, vol. 1, p. 782. Oct. 23, 2002.
Khetani S.R. et al., Hepatology, 40(3) pp. 545-554. Sep. 2004.
Lipshutz R.J. et al. *Nature Genetics*, vol. 21, (Supp) pp. 20-24. Jan. 1, 1999.
Fabrega, Alfredo J. et al., "Cationic lipid-mediated transfer of the hiL-10 gene prolongs survival of allogeneic hepatocytes in nagase analbuminemic rats 1,2," Transplantation, vol. 62(12):1866-1871 (1996).
Lecouter, Jennifer et al., "Angiogenesis-Independent Endothelial Protection of Liver: Role of VEGFR-1," Science, vol. 299(5608):890-893 (2003).
European Office Action for Application No. 05804091.6, pp. 1-9, dated Dec. 30, 2011.

*Primary Examiner* — Daniel C Gamett
(74) *Attorney, Agent, or Firm* — Nelson Mullins Riley & Scarborough LLP; Debra J. Milasincic, Esq.

(57) ABSTRACT

This invention relates to methods to stabilize and/or improve the function of parenchymal cells. Also provided are systems of co-cultures of hepatocyte-stabilizing non-parenchymal cells used in bioreactor microenvironments to identify hepatic stabilizing factors by gene-expression profiling.

9 Claims, 9 Drawing Sheets

(Murine fibroblasts cultured on collagen in hepatocyte medium to mimic co-culture conditions)

| Acc.# | Description | mRNA Expression level | | |
|---|---|---|---|---|
| | | 3T3-J2 | NIH-3T3 | MEF |
| M31131 | N-cadherin | 423 | 542 | 920 |
| X59990 | α-catenin 1 | 605 | 860 | 936 |
| M90365 | Plakoglobin (PG) | 28 | 75 | 520 |
| M90364 | β-catenin | 1788 | 1826 | 2155 |
FIG. 4A
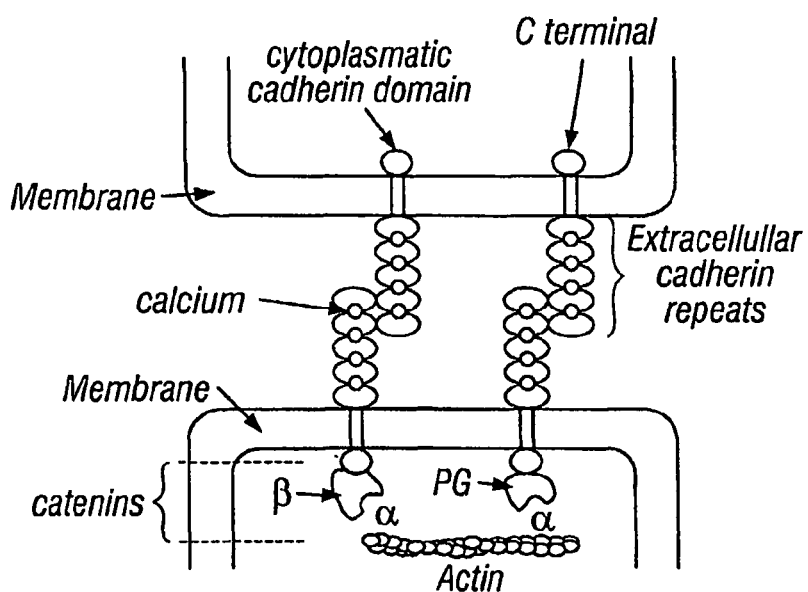
FIG. 4B
Hepatocyte-Fibroblast N-cadherin    Hepatocyte-Hepatocyte β-cadherin
 
Hepatocyte-Hepatocyte N-cadherin    Hepatocyte-Fibroblast β-cadherin
FIG. 4C

Freshly Isolated Hepatocytes

Pure Hepatocytes-2 weeks

Hepatocyte-3T3 co-cultures

MOLECULES WITH EFFECTS ON CELLULAR DEVELOPMENT AND FUNCTION

CROSS REFERENCE TO RELATED APPLICATIONS

This application is a National Stage application filed under 35 U.S.C. §371 and claims priority to International Application No. PCT/US2005/027604, filed Aug. 4, 2005, which application claims priority to U.S. Provisional Application No. 60/599,402, filed on Aug. 5, 2004, the disclosures of which are incorporated herein by reference.

STATEMENT AS TO FEDERALLY-SPONSORED RESEARCH

The invention was made in part with funds from the National Institutes of Health, Grant No. DK065152. The U.S. Government may have certain rights in the invention.

TECHNICAL FIELD

This invention relates to methods and compositions to stabilize and/or improve the function of parenchymal cells and stem cells including, but not limited to, hepatocytes, hepatocyte-like cells, and progenitor cells. Also provided are systems of co-cultures of hepatocyte-stabilizing non-parenchymal cells used in bioreactor microenvironments as well as methods and systems used to identify parenchymal cell stabilizing factors by gene-expression profiling.

BACKGROUND

The development and function of tissues depend on interactions between non-parenchymal and parenchymal cells to modulate differentiation, proliferation, and migration. Specifically, parenchymal-non-parenchymal interactions are important in physiology, pathophysiology, cancer, development, and in attempts to replace tissue function through 'tissue engineering'. While the functional importance of such cell-cell interactions is well established in many systems, the underlying molecular mechanisms often remain elusive. Parenchymal cells interact with extracellular matrix materials, non-parenchymal cells and soluble signals to properly differentiate and maintain parenchymal cell functions. A great deal of study has been dedicated to the identification of extracellular matrix materials that play a role in parenchymal tissue development and maintenance. Such studies have elucidated the role of certain factors in parenchymal cell maintenance and development, however, there remains many unanswered questions as to the role of soluble factors and membrane bound interactions with non-parenchymal cells in the development of tissue, tissue maintenance and tissue growth.

The 'feeder layer' effect is widely used in stem cell culture and the culture of many tissue types (skin, liver, pancreas, muscle and the like). This is often used as a generic support of differentiated (or self renewing) cells much in the way serum is a generic additive for cell culture. Identification of the factors (soluble or insoluble) would be important for laboratory and therapeutic applications.

The liver is the heaviest gland of the body, weighing about 1.4 kg (about 3 lb) in the average adult, and is the second largest organ after the skin. The lobes of the liver consist of many functional units called lobules. Each lobule consists of specialized epithelial cells, called hepatocytes (i.e., parenchymal cells), arranged in irregular, branching, interconnected plates around a central vein, the sinusoids, through which blood passes.

The liver's main function is to control the level of particular substances in the blood. For instance, the liver plays a major role in carbohydrate metabolism by removing glucose from the blood, under the influence of the hormone insulin, and storing it as glycogen. When the level of glucose in the blood falls, the hormone glucagon causes the liver to break down glycogen and release glucose into the blood. The liver also plays an important role in protein metabolism, primarily through deamination of amino acids, as well as the conversion of the resulting toxic ammonia into urea, which can be excreted by the kidneys. The liver also detoxifies many drugs and hormones. In addition, the liver participates in lipid metabolism by storing triglycerides, breaking down fatty acids, and synthesizing lipoproteins. The liver also secretes bile, which helps in the digestion of fats, cholesterol, phospholipids, and lipoproteins; and stores vitamins (A, $B_{12}$, D, E, and K) and minerals (iron and copper). Furthermore, the Kupffer's cells of the liver phagocytize worn-out red and white blood cells as well as some bacteria. Bilirubin, a breakdown product of heme, is excreted by the liver into the bile ducts where it passes into the intestinal tract.

There are many different causes of liver disorders. Hepatitis, an inflammation of the liver, is commonly caused by alcoholism or other toxic ingestion, or infection by viruses or other parasites. Cirrhosis of the liver is marked by the destruction of parenchymal cells and their replacement with connective tissue. Hepatitis resulting from infection by hepatitis C virus, for example, often develops into cirrhosis. Hepatitis B virus infection, on the other hand, is strongly believed to lead in many cases to liver cancer (hepatoma). Hepatoma can also be caused by the activation of endogenous oncogenes, through exposure to carcinogens, for example.

Severe forms of these disorders may result in chronic or acute hepatic failure. Fulminant hepatic failure (FHP) is associated with massive necrosis of hepatocytes and concomitant sudden severe impairment of hepatic metabolism. Partial or total liver replacement is needed in case of transient or permanent failure of vital liver functions.

The liver has a remarkable-capacity to regenerate. In the rat, for example, a 70% hepatectomized liver will regenerate its original mass in about seven days. Nonetheless, because the liver carries out so many important biochemical functions, severe liver damage or loss of the liver is rapidly fatal. Some efforts have been made, therefore, to identify the molecular factors involved in the liver regeneration process.

Most previous studies have focused on events occurring in the first few (e.g., 1-6 hours) hours after surgery. Identifying genes that regulate hepatocyte fate and function (i.e., proliferation and differentiation) has been very difficult. One study examined hepatocyte proliferation in an in vivo regeneration model. In this regard, Hagiya et al., 1994, Proc. Natl. Acad. Sci. USA 9:8142-8146, cloned ALR (augmenter of liver regeneration) from rat; Hsu et al., 1992, Mol. Cell Biol. 12:4654-4665, identified a gene encoding a novel leucine-zipper containing protein termed liver regeneration factor-1 (LRF-1); and Mohn et al., 1991, Mol. Cell Biol. 11:381-390, identified 41 novel immediate-early partial DNA sequences. These genes were isolated by examining expression during early time periods following partial hepatectomy (e.g., 1-6 hr). During this early stage of regeneration, the expression of acute phase inflammatory proteins is substantially high, thereby yielding a "background" of induced expression of genes which are not very useful because their expression is not specific to liver regeneration. This approach is limited for several reasons: (i) it is not causal, there is no way to filter the genes to establish a relationship to hepatocyte fate (i.e., pro- or anti-regenerative), (ii) changes in gene expression are combined for all cell types in the liver (hepatocytes and others, which comprise 33% of the liver), and (iii) there is large variability between animals. Overcoming this lack of specificity may be a determining factor in obtaining urgently needed tools for early diagnosis of liver disorders, as well as improvements in therapy that take advantage of the liver's unusual regenerative capacity.

SUMMARY

The disclosure provides a gene expression profiling approach to facilitate the study of cell-cell interactions. The non-parenchymal gene expression data can also be utilized to identify candidate genes in diverse areas such as the self-renewal of embryonic stem cells on non-parenchymal feeder layers and differentiation of keratinocytes on fibroblasts.

The invention provides a method of identifying molecular mediators that define a functional profile for a parenchymal cell population. The method comprises (a) obtaining a first profile of a co-culture of a parenchymal cell population and a first non-parenchymal cell population, comprising measuring a tissue-specific function of the parenchymal cells and correlating the tissue-specific function with a gene expression profile of the first non-parenchymal cell population; (b) obtaining a second profile of a co-culture of the parenchymal cell population and a second non-parenchymal cell population, comprising measuring the tissue-specific function of the parenchymal cells and correlating the tissue-specific function with a gene expression profile of the second non-parenchymal cell population; (c) generating a functional profile, comprising: (i) identifying a change in the tissue-specific function; (ii) comparing the first and second gene expression profiles to identify one or more gene expression differences; and (iii) correlating the one or more genes with the change in the tissue specific function, wherein the function profile comprises the identity of candidate molecular mediators.

The invention also provides a database comprising a computer readable list of the functional profile obtained from the method described herein.

The invention also provides a method for screening a compound for an affect on parenchymal cell function. The method comprises contacting a parenchymal cell culture system with a test compound or agent and measuring expression of one or more molecular mediators set forth in a functional profile for the parenchymal cell type being tested.

The invention also provides a method of treating a subject having a liver disease or disorder comprising administering a molecular mediator or an agent that promotes production of a molecular mediator identified by the method of the invention, wherein the molecular mediator has a positive effect on hepatic cell function. In one aspect, the molecular mediator is T-cadherin.

The invention further provides a method of treating a subject having a liver disorder comprising administering an inhibitor of a molecular mediator identified by the method of the invention, wherein the molecular mediator has a negative effect on hepatic cell function.

Also provided by the invention is a method of culturing hepatic cells. The method comprises contacting the hepatic cells with a gene or gene product identified by the method of the invention (e.g., those set forth in Table 1).

The invention provides a co-culture comprising: a parenchymal cell population; and a support cell population, wherein the support cell population is transfected or transformed with a polynucleotide encoding a molecular mediator identified by the method of the invention, wherein the molecular mediator has a positive effect on the parenchymal cell function.

The invention further provides a method of promoting hepatic cell function comprising culturing a hepatic cell with an agent that promotes expression of a molecular mediator, wherein the molecular mediator is identified by the method of invention and wherein the molecular mediator has a positive effect on hepatic cell function.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A-C shows an analysis of the cadherin pathway suggesting a negative correlation with hepatocyte function. Since the expression profile of plakoglobin (PG), which interacts with cadherins, correlated negatively with inductive ability of fibroblasts in unsupervised analysis, expression profiles of other constituents of the cadherin pathway were checked and found to be similar to that of PG. Values indicate average of duplicate samples, scaled to an intensity of 200. B. Classical cadherins are transmembrane proteins whose cytoplasmic domains anchor to the actin cytoskeleton by interacting with various signaling molecules such as β-catenin, plakoglobin (γ-catenin), and α-catenin. C. Immunofluorescent staining of N-cadherin (top) and β-catenin (bottom) demonstrate protein expression and localization at both homotypic and heterotypic cell-cell junctions in hepatocyte co-cultures.

Nuclei are counterstained with Hoechst. Representative staining is shown for 3T3 (medium inducers) co-cultures, but protein localization was seen in all co-cultures.

Figure 5A:
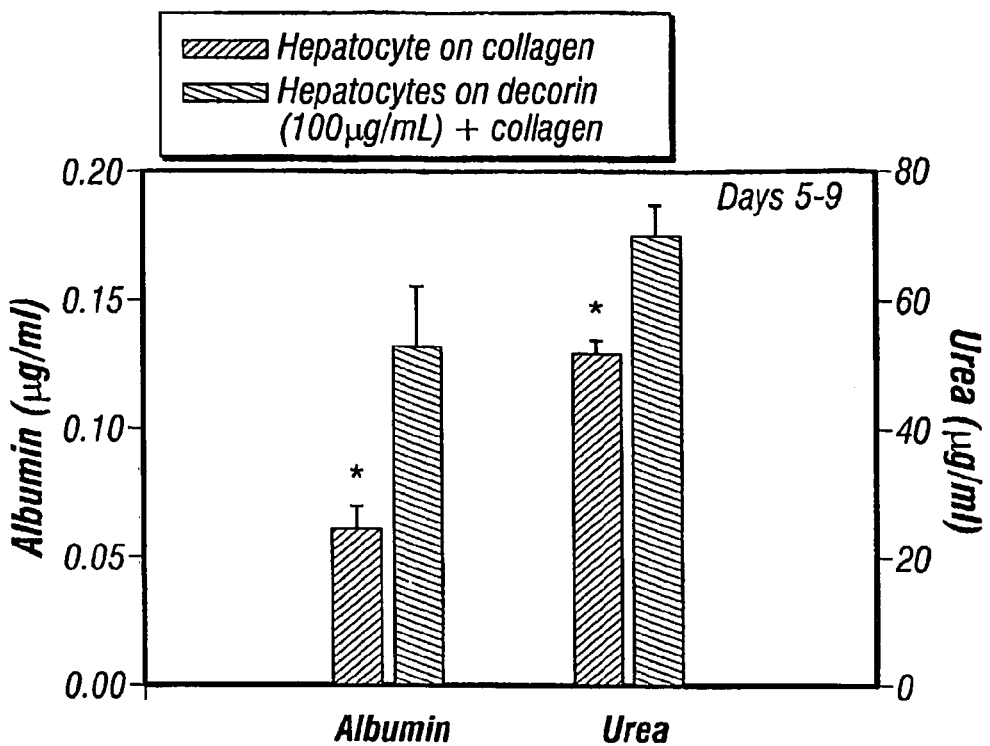
Figure 5B:
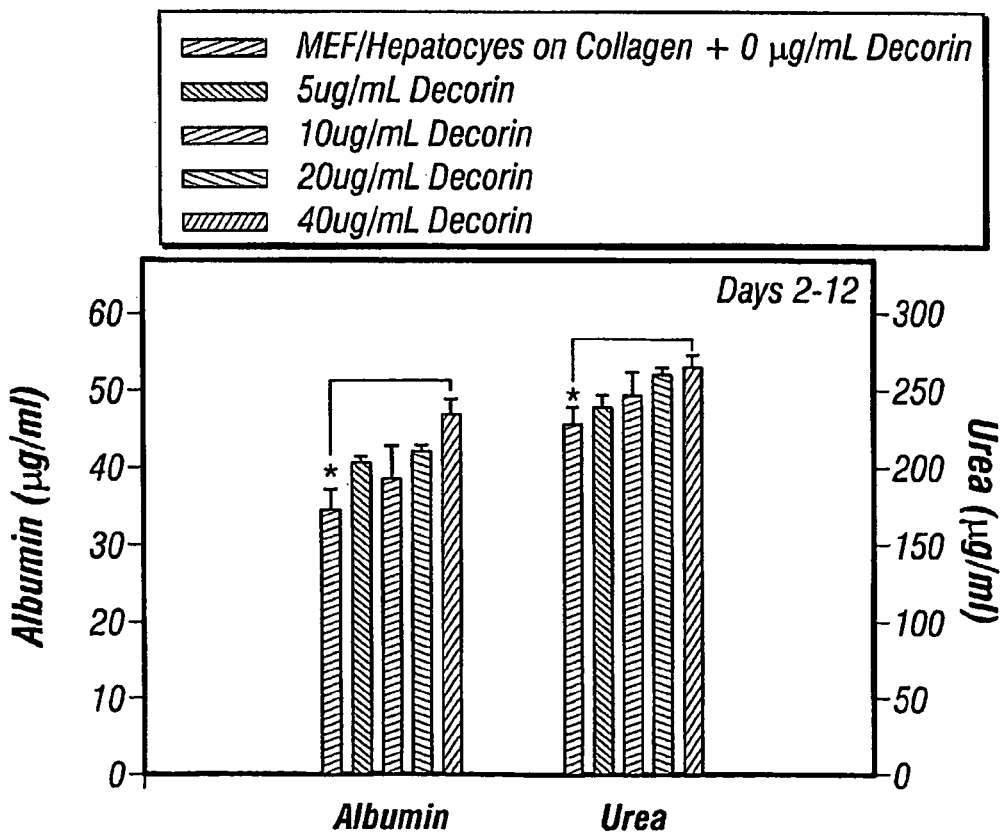

FIG. 5A-B show the validation of extracellular matrix, decorin, as a potential mediator of cell-cell interaction. A. Upregulation of total urea and albumin production in hepatocytes plated alone on adsorbed decorin (summation over days 5-9). B. Dose-dependent upregulation of total hepatic functions in co-cultures of hepatocytes and low function-inducing mouse embryonic fibroblasts (summation over days 2-12) on adsorbed decorin. * $p<0.05$ (two-tailed Student's t-test). Error bars represent standard error of the mean (n=3).

Figure 6:
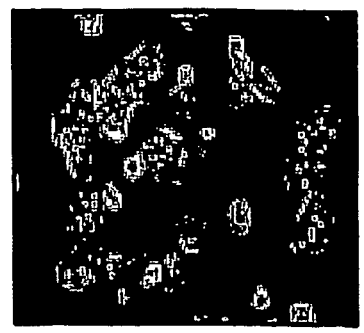
Figure 6:
Figure 6:
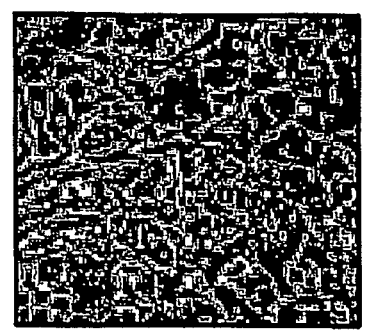
Figure 6:
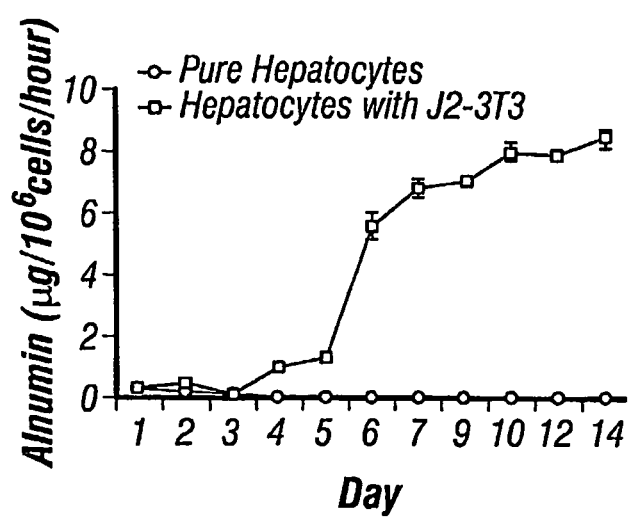

FIG. 6 shows co-cultivation of hepatocytes with murine embryonic J2-3T3 fibroblasts. A graph depicts albumin production in pure hepatocytes compared to co-cultures of hepatocytes with a fibroblast cell line.

Figure 7:
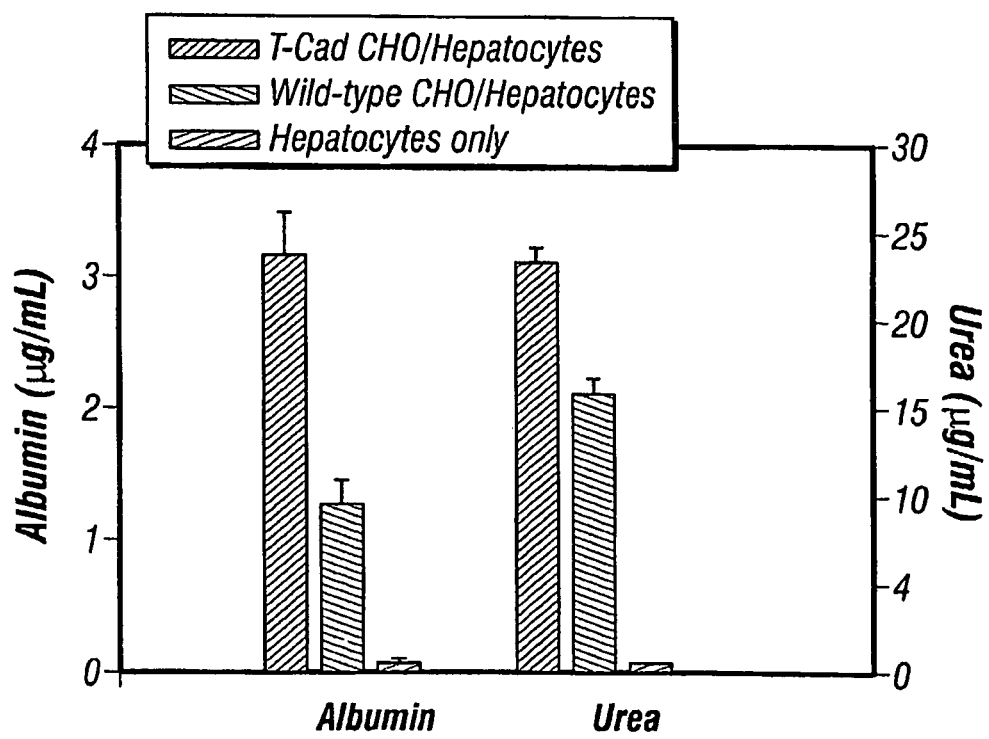

FIG. 7 is a graph depicting co-cultivation of hepatocytes with transformed CHO cells expressing T-cadherin and the induction of albumin production by hepatocytes in co-culture.

Figure 8:
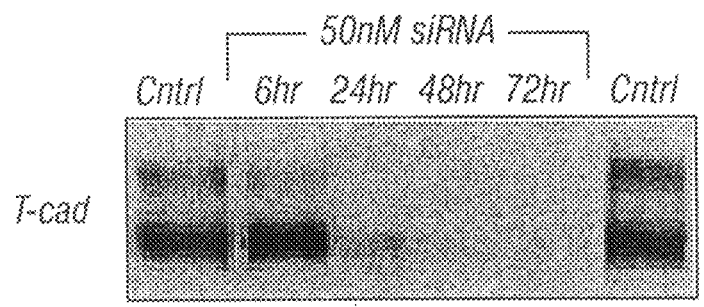

FIG. 8 is shows a Western blot showing T-cadherin expression in the presence of 50 nM siRNA.

Figure 9:
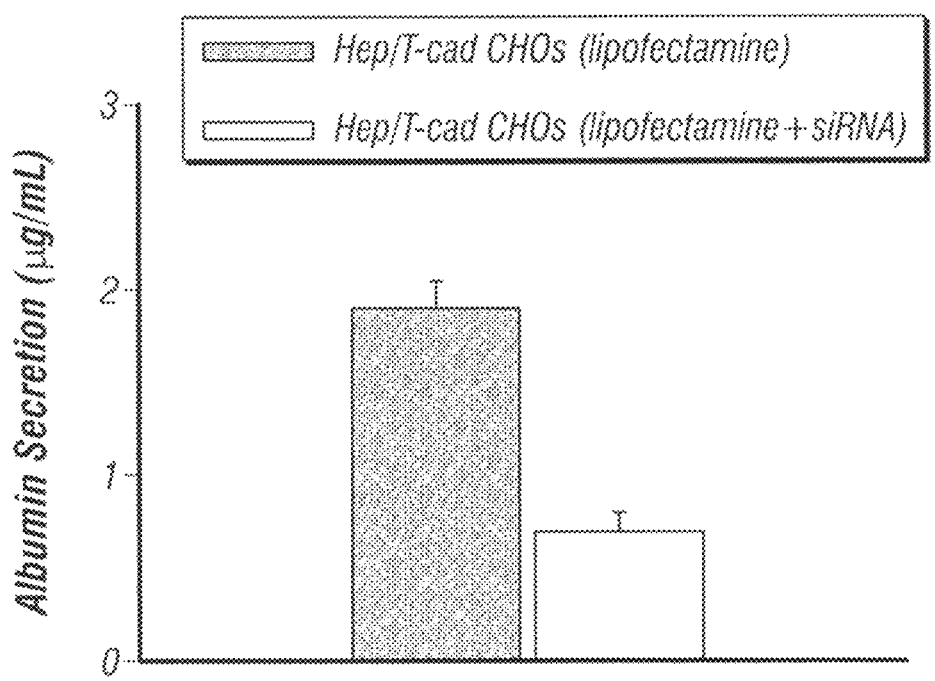

FIG. 9 is a graph showing albumin production by hepatocytes in co-culture with CHO cells transfected with T-cadherin in the presence and absence of siRNA.

Figure 10:
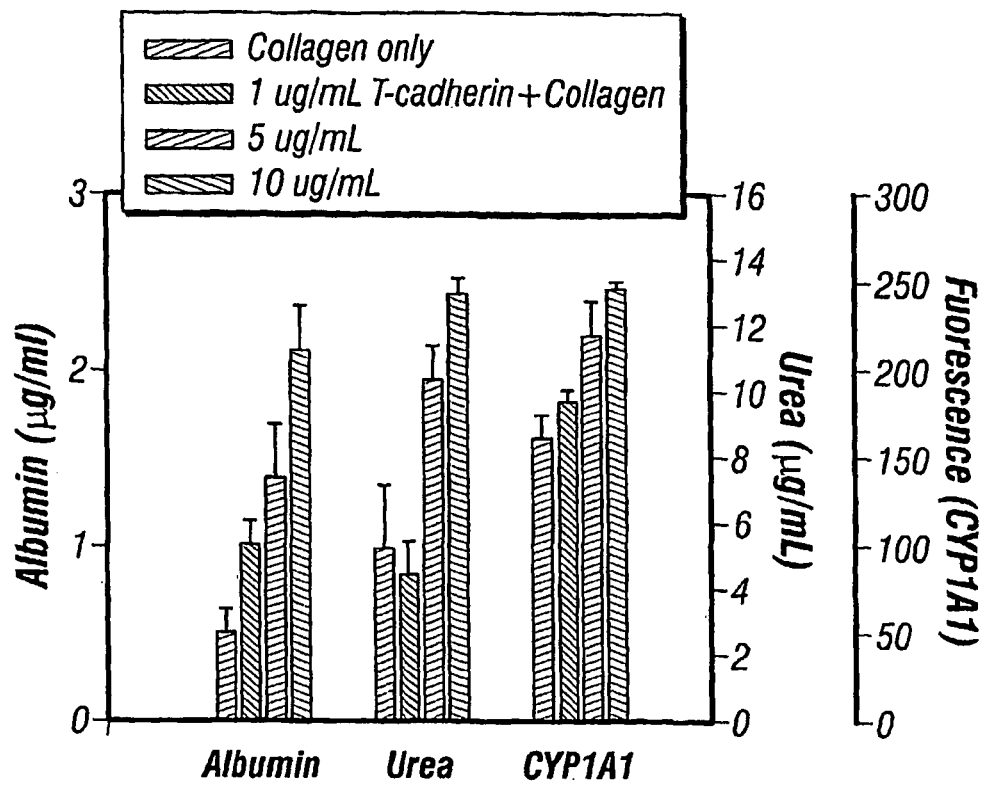

FIG. 10 is a graph showing the effect T-cadherin has on albumin expression and urea production by hepatocytes. A dose dependent effect is demonstrated.

Figure 11:
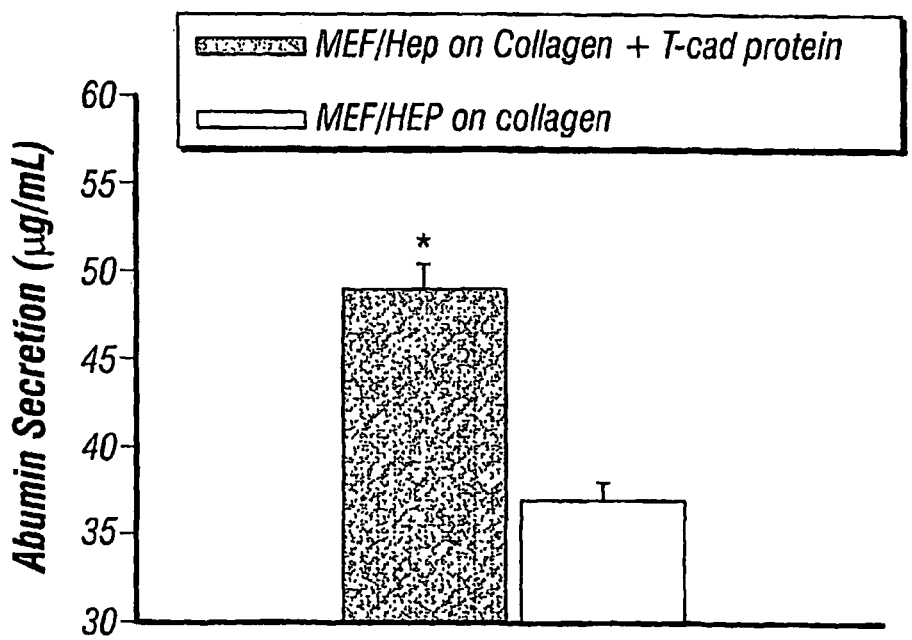

FIG. 11 is a graph demonstrating the effect of T-cadherin in co-cultures of hepatocytes and MEF.

DETAILED DESCRIPTION

The development and function of tissues depend on interactions between non-parenchymal and parenchymal cells to modulate differentiation, proliferation, and migration. Specifically, parenchymal/non-parenchymal interactions are important in physiology, pathophysiology, cancer, development, and in attempts to replace tissue function through 'tissue engineering'. While the functional importance of such cell-cell interactions is well established, the underlying molecular mechanisms remain elusive. Investigation of these phenomena is further confounded by the diversity of supportive cell types (e.g., stromal/non-parenchymal cells) found in organs. For example, fibroblasts are often classified together based on their morphology, mesenchymal markers, and adherence to tissue culture plastic; however, even fibroblasts in a single organ can vary significantly in their transcriptional profiles. Even though such dramatic transcriptional variations in non-parenchymal cells would be expected to impact their interaction with surrounding parenchymal cells, a correlation of non-parenchymal gene expression with parenchymal cell function has not been systematically explored. Such correlative data offers insight into the underlying mechanisms of cell-cell interaction in a given tissue.

In the era of genomic medicine, biomedical phenomena may be investigated via global analyses rather than through the study of individual molecular species. This systems-level approach has been used to stratify clinical trials and predict metastatic potential of tumors. The disclosure provides a functional genomic approach to explore the mechanisms of cell communication in parenchymal/non-parenchymal cell interactions. Functional outcomes were scored and correlated with patterns of gene expression in a manner that can be generalized to the study of a variety of biological phenomena. Primary parenchymal cells were co-cultured with various non-parenchymal cell lines (NPCs) to produce variable induction of tissue/parenchymal-specific functions. Non-parenchymal genes whose expression correlated positively (i.e., stimulatory) and negatively (i.e., inhibitory) with the functional profile were catalogued. Using this approach, a number functionally characterized candidates were identified in a liver model of the invention. The candidates were in the relevant cell communication categories (cell surface, matrix, secreted factors). Using the methods of the disclosure a database was generated and provides the first global molecular definition of a hepatocyte-stabilizing non-parenchymal microenvironment. Thus, the disclosure provides methods, systems, and useful data of candidate molecular mediators that play a role in induction of parenchymal cell function (e.g., liver-specific functions). The information provides methods and compositions that can be used in stabilizing tissue/parenchymal specific functions in vitro and in vivo.

For example, in vivo liver development requires interaction of the endodermal hepatic bud with the surrounding mesenchyme, with soluble signals FGF-2 and BMP-4 being essential for early development. However, cell-cell contact through unknown mediators is also required for further liver development. In vitro, co-cultivation of primary hepatocytes with a plethora of distinct non-parenchymal cell types from different species and organs has been shown to support differentiated hepatocyte function in a manner reminiscent of hepatic organogenesis. These hepatocyte co-cultures have been used to study various aspects of liver physiology and pathophysiology such as lipid metabolism, and induction of the acute-phase response. This area of investigation has gained particular interest due to its relevance to both hepatic tissue engineering and development of in vitro models for pharmaceutical drug screening.

Conventional approaches to investigate mechanisms of cell-cell interaction have included conditioned media and transwell culture. In hepatocyte co-cultures, these techniques have recently been supplemented with microfabrication-based patterning tools that provide additional insight into mechanisms of cell-cell communication. Despite the progress in available technology to study such parenchymal-non-parenchymal interactions, examination of potential molecular mediators in hepatocyte co-cultures has generally progressed through serial investigation of individual candidates. In the era of functional genomics, the opportunity now exists to correlate global patterns of gene expression with functional responses resulting from cell-cell interaction. The use of DNA microarrays coupled with bioinformatic tools offer the ability to perform quantitative, parallel measurements of gene expression.

Despite significant investigation, a complete picture of the molecular mediators of parenchymal-non-parenchymal interaction is unavailable. For example, the molecular mediators in hepatocyte co-cultures with non-parenchymal cells is unavailable. The methods of the invention have provided the ability to identify a number of molecular mediators. For example, using the methods of the invention promising candidate molecular mediators were identified in the co-culturing of hepatocytes with fibroblast cells. A few mediators include, for example, E-cadherin, T-cadherin and liver regulating protein (LRP); however, non-parenchymal cells lacking E-cadherin and LRP retain the ability to support hepatic functions, suggesting that neither is the sole mediator of the 'co-culture effect'. Indeed, it is likely that several distinct mechanisms cooperate to modulate parenchymal cell (e.g., hepatocyte) function in co-cultures. Nevertheless, at least some of these multifactorial mechanisms appear to be highly conserved in mammals.

Such molecular mediators play a role in primary hepatocytes function from a variety of species (i.e. human, rat, mouse, porcine) and are stabilized to different extents by non-parenchymal cells from different species, tissues or embryological origin (epithelial or mesenchymal). Thus, identification of a set of non-parenchymal-derived signals that support parenchyma cell (e.g., hepatocyte) differentiation would have broad fundamental and technological implications.

The invention provides methods and systems for the identification of molecular mediators of parenchymal cell function, maintenance and/or differentiation. The invention also provides a set of molecular mediators (e.g., genes and polypeptides) that improve the function of parenchymal cells (e.g., hepatocyte or hepatocyte-like cells) as well as a set of molecular mediators (e.g., genes and polypeptides) that inhibit the function of parenchymal cells (e.g., hepatocyte or hepatocyte-like cells). The set of such molecular mediators is referred to herein as a functional profile. Such molecular mediators function to change the activity profile of a parenchymal cell-type.

In one aspect of the invention polynucleotides and their encoded polypeptide products (collectively and individually molecular mediators) were identified as stimulators or inhibitors of hepatocyte function in a model system of the invention. The polypeptides have use in a number of embodiments: (i) cell-based therapies—the polypeptide can be used to stabilize hepatocytes for tissue engineered livers, bioartificial liver devices, and the like; (ii) in in vitro models—these polypeptides may improve the function of in vitro liver models for drug testing, development of antiviral therapies, or environmental toxicity; (iii) in clinical therapeutics—these polypeptides may act as 'hepatoprotectants' to improve recovery of injured liver (for clinical hepatoprotectants, these polypeptides and polynucleotides offer a new set of potential therapeutics—others have largely been empirically determined (such as IL-6) or studied in transgenic animals); (iv) in stem cell differentiation—these polypeptides may act to drive embryonic or adult stem cells in vitro or in vivo to differentiate more efficiently along the hepatocyte lineage; (v) in cell line maintenance—these molecules may act to improve the function of immortalized cell lines that are commercially available. For example, these polypeptides can replace the need for co-cultivation with another cell type in tissue engineered devices or bioartificial livers; and (vi) cell function measurements—The polypeptides and polynucleotides can be used as a measure of hepatic function and associated diseases and disorders.

"Non-parenchymal" cells include stromal cells (e.g., fibroblasts) with or without other cells and/or elements found in loose connective tissue, including but not limited to, endothelial cells, pericytes, macrophages, monocytes, plasma cells, mast cells, adipocytes and the like. Stromal cells generally form support for tissue specific cells. Typically stromal cells are not tissue-specific but are rather ubiquitous in all tissues of the body. The most common type of stromal cell is the fibroblast. In tissue culture, the stromal cells are often referred to as "feeder layers". Examples of commonly used fibroblast cell lines include 3T3-J2, NIH-3T3, and Mouse Embryonic Fibroblasts. For example, murine embryonic fibroblasts (MEF) are commonly used as a feeder layer. Prior to co-culture, the MEF may be irradiated (levels of between 35-50 gray) to reduce cell proliferation without compromising metabolic function (Shamblott et al. 1998, Proc Natl Acad Sci USA 95:13726-13731; Amit et al. 2000, Dev Biol 227: 271-278); however, various chemicals/drugs (e.g., chemotherapeutic drugs) can achieve similar results. Parenchymal cells are then plated onto a MEF feeder layer culture (Reubinoff et al. 2000, Nature Biotechnology 18:399-404; Thomson et al. 1998, Science 282:1145-1147).

Tissue-specific or parenchymal cells comprise the cells which form the essential and distinctive tissue of an organ as distinguished from its supportive framework. The parenchymal cell type used in the invention will depend upon the tissue to be cultured, which may include, but is not limited to, bone marrow, skin, liver, pancreas, kidney, neurological tissue, and adrenal gland, to name but a few. Although the invention is described using the specific example of hepatocytes, the methods and compositions of the invention are applicable to other parenchymal cell types derived from the various tissues of the body.

The invention provides a gene expression profiling approach to identify non-parenchymal genes that may modulate parenchymal cell function. A 'functional profile' of cell-cell interaction is established by measurement of parenchymal-specific functions in parenchymal cells (e.g., hepatocytes) upon co-cultivation with at least two non-parenchymal cells (e.g., several closely related murine fibroblasts), which are scored as high inducers, medium inducers, or low inducers of parenchymal (e.g., hepatic) function. Gene expression profiles are obtained for each non-parenchymal cell type and correlated with the parenchymal cell functional measurement (e.g., a parenchymal cell specific activity). The parenchymal cell specific activity will vary with respect to each non-parenchymal cell type. A functional profile is then made using a comparison of the profiles from each non-parenchymal cell type. In one aspect, the non-parenchymal cells used for gene expression profiling are those that have undergone co-cultivation with a parenchymal cell type (e.g., hepatocytes). However, pure fibroblast cultures can be used in identifying candidate genes involved with induction of parenchymal cell functions. Experimental evidence suggest that nonviable non-parenchymal feeder layers (irradiated, desiccated, fixed, mitomycin-C treated) elicit comparable responses to viable non-parenchymal cells, lending support to the idea that at least some non-parenchymal-derived signals do not require reciprocal signaling. In another aspect, pure non-parenchymal cell cultures are treated to mimic, as closely as possible, other aspects of the co-culture environment (e.g., are treated with media formulation and matrix coating) to obtain a set of candidates that are involved with the functional outcomes. The number of non-parenchymal cell types used in the methods of the invention comprises at least two non-parenchymal cell types. Typically the non-parenchymal cell types will induce a high and low parenchymal cell specific activity, respectively. However, the differences can be high-high, medium-high, medium-medium, low-medium and low-low. Typically the difference in parenchymal cell activity during co-culture with the non-parenchymal cells need only be a measurable difference.

Accordingly, the invention provides a method of identifying molecular mediators of tissue development and modulation, comprising obtaining a first gene profile of a co-culture of a parenchymal cell population and a first non-parenchymal cell population by measuring a tissue-specific function of the parenchymal cells and correlating the tissue-specific function with a gene expression profile of the first non-parenchymal cell population. At least two non-parenchymal cell types are used, thus the method includes obtaining a second gene profile of a co-culture of the parenchymal cell population and a second non-parenchymal cell population by measuring the tissue-specific function of the parenchymal cells and correlating the tissue-specific function with a gene expression profile of the second non-parenchymal cell population. A functional profile is generated by identifying a change in the tissue-specific function comparing the first and second gene expression profiles to identify one or more gene expression differences and correlating the one or more genes with the change in the tissue specific function, wherein the function profile comprises the identity of candidate molecular mediators.

In another aspect, the invention provides a functional genomic approach utilizing gene expression profiling to identify molecular mediators of non-parenchymal cells involved in induction of liver-specific functions. Functional responses are correlated with fibroblast gene expression profiles obtained using gene chip microarrays. Microarray data analysis of the gene expression profiles identifies candidate genes in the cell communication category (e.g., cell surface, extracellular matrix, secreted factors) that are involved in induction of hepatic functions. Further analysis using various databases (e.g., PubMed, GenBank) facilitates prioritization of candidates for functional characterization.

A functional profile is generated by obtaining a first gene profile from co-culture of a parenchymal cell population and a first non-parenchymal cell population by measuring a tissue-specific function of the parenchymal cells and correlating the tissue-specific function with a gene expression profile of the first non-parenchymal cell population; and obtaining a second gene profile of a co-culture of the parenchymal cell population and a second non-parenchymal cell population by measuring the tissue-specific function of the parenchymal cells and correlating the tissue-specific function with a gene expression profile of the second non-parenchymal cell population. A functional profile is generated by identifying a change in the tissue-specific function and comparing the first and second gene expression profiles to identify one or more gene expression differences and correlating the one or more genes with the change in the tissue specific function, wherein the functional profile comprises the identity of candidate molecular mediators.

The choice of non-parenchymal cells used in the methods of the invention will depend upon the parenchymal cell types used. For example, a variety of both liver and non-liver derived non-parenchymal cells have been reported to induce hepatic function in co-culture. Furthermore, induction has been reported by non-parenchymal cells (both primary and immortalized) derived from a different species than the primary hepatocytes, suggesting possible conservation of underlying mechanisms. The ready availability and ease of culture of immortalized murine fibroblasts has led to a resurgence of interest in their influence on parenchymal cell (e.g., hepatocyte) functions for applications in tissue engineering and bioreactor development including, but not limited to, bioartificial liver devices.

The disclosure demonstrates co-culture-mediated stabilization of parenchymal and non-parenchymal cells from the same and different species. For example, the disclosure demonstrates co-culture stability of hepatocytes from the same species (mouse) and another species (human) as the fibroblasts. In addition, since 3T3 and primary murine embryonic fibroblasts are commonly used as supporting feeder layers in other organ systems, the gene expression data acquired are useful in a number of other applications. Accordingly, the role of candidate genes elucidated in murine fibroblast cell lines in non-parenchymal cells of the liver can be obtained (e.g. sinusoidal endothelial cells).

Fibroblast gene expression profiles can be obtained any number of ways, but will typically be obtained via gene chips (e.g., Affymetrix GeneChips™) and correlated with the parenchymal cell functional activity. In one aspect of the invention, a functional profile is obtained using data analysis of gene chip data. For example, the non-parenchymal cell expression profile can be reduced by eliminating overlapping genes and focusing on genes that do not overlap or which are expressed at different levels. Using such methods, the non-parenchymal gene profiles obtained from hepatocyte co-cultures were reduced from ~12000 fibroblast genes and expressed sequence tags to a handful of candidate genes that modulate hepatocyte function in co-cultures. Candidates were chosen for testing as examples and were subsequently shown to play a role in parenchymal/non-parenchymal interaction in the model system of the invention, thereby validating the approach. Ultimately, the functional genomic approach presented here can serve as a general tool to facilitate mechanistic study of cell-cell interactions in diverse fields such as tissue engineering, stem cell biology, and cancer.

Using the methods and systems of the invention a number of functionally characterized candidate genes and gene products (i.e., polypeptides) in the cell communication category (cell surface, extracellular matrix, secreted factors) that are involved in induction of hepatic functions were identified. For example, the cell surface protein, N-cadherin, was localized to hepatocyte-fibroblast borders, while adsorbed decorin upregulated hepatic functions in pure cultures as well as in co-cultures with low-inducing fibroblasts. T-cadherin was also demonstrated to play a role in hepatocyte function (e.g., albumin production).

Utilizing the gene expression profiling approach described herein the disclosure demonstrates that expression of truncated-cadherin (T-cad) in 3T3 fibroblasts stabilizes hepatocytes. Cadherins mediate cell-cell interactions in tissues throughout the body. Cadherins are commonly expressed in multiple tissues of the body. For example, Neural-cadherin (N-Cadherin), Epithelial-cadherin (E-Cadherin), and Liver-Intestine-cadherin are all expressed in the developing and adult liver. Sinusoidal endothelial cells express Vascular-Endothelial cadherin and cholangiocytes (bile ductal cells) express E-cadherin. Though the role of cadherins in hepatocyte/non-parenchymal co-cultures is largely undiscovered, evidence shows that E-cadherin expression in L929 fibroblasts positively correlates with hepatocyte functions. T-cad lacks an intracellular domain, is linked to the cell membrane via a glycosyl phosphtidyl inositol (GPI) moiety. As described in the Examples below T-cadherin stimulates hepatocyte specific activity alone or when transfected into a support cell.

The functional profiles generally categorize candidate genes/molecular mediators into two groups (positive or negative correlations with induction profiles) based on the premise that 'low inducer' fibroblasts could, in fact, be actively inhibiting hepatocyte function. Of the functionally characterized candidates in the cell communication category obtained in using the methods of the disclosure, three candidates were experimentally validated. Gene expression of decorin, an extracellular matrix proteoglycan, correlated positively with inductive activity. Experimentally, it was confirmed that decorin did indeed induce liver functions in both pure hepatocyte cultures and in co-cultures of hepatocytes with fibroblasts that had 'low' inductive activity (see, e.g., FIG. 5). Despite decorin's inductive ability, neither culture achieved maximal production rates of hepatic markers (as with 3T3-J2s) due to the addition of decorin alone. These data serve to validate the gene expression profiling approach and confirm the hypothesis that cell-cell interaction is likely to be multifactorial. Analysis of the cadherin pathway emerged from the identification of plakoglobin (γ-catenin) as a candidate.

N-cadherin, β-catenin, expression profiles also correlated negatively with inductive activity. The localization of N-cadherin and β-catenin at heterotypic (fibroblast/hepatocyte) junctions was confirmed using immunofluorescence (see, e.g., FIG. 4), providing the first evidence of functional communication between the cell types. In contrast, other groups have shown a positive inductive role for E-cadherin. Interaction between N- and E-cadherin pathways has also been reported.

Parenchymal cells can be obtained from a variety of sources including, but not limited to, liver, skin, pancreas, neuronal tissue, muscle, and the like. Such parenchymal cells can be obtained by biopsy or from cadaver tissue. For example, in vitro cultures of liver cells have been prepared from humans as well as from experimental animals. Primary cultures of rat hepatocytes have been used extensively to study the effects of potential toxins on enzyme leakage, metabolism, and cellular membranes (Grisham, 1979, Int. Rev. Exp. Pathol. 20:123-210; Acosta and Mitchell, 1981, Biochem. Pharmacol. 30:3225-3230).

Hepatocytes may be isolated by conventional methods (Berry and Friend, 1969, J. Cell Biol. 43:506-520) which can be adapted for human liver biopsy or autopsy material. Briefly, a cannula is introduced into the portal vein or a portal branch and the liver is perfused with calcium-free or magnesium-free buffer until the tissue appears pale. The organ is then perfused with a proteolytic enzyme such as a collagenase solution at an adequate flow rate. This should digest the connective tissue framework. The liver is then washed in buffer and the cells are dispersed. The cell suspension may be filtered through a 70 μm nylon mesh to remove debris. Hepatocytes may be selected from the cell suspension by two or three differential centrifugations.

For the isolation of human hepatocytes perfusion of individual lobes of excised human liver using HEPES buffer may be performed. Perfusion of collagenase in HEPES buffer may be accomplished at the rate of about 30 ml/minute. A single cell suspension is obtained by further incubation with collagenase for 15-20 minutes at 37° C. (Guguen-Guillouzo and Guillouzo, eds, 1986, "Isolated and Culture Hepatocytes" Paris, INSERM, and London, John Libbey Eurotext, pp. 1-12; 1982, Cell Biol. Int. Rep. 6:625-628).

The isolated hepatocytes may then be used in a co-culture with non-parenchymal cells (e.g., CHO cells, fibroblasts and the like). Such co-cultures comprise a microenvironment conducive to expression of liver-specific metabolic activity as and/or hepatic cell proliferation. Hepatic cell functional activity can be examined by measuring the synthesis of, for example, albumin, fibrinogen, transferrin and other proteins, and display TCDD-inducible cP450 activity. Such activity is then correlated with a gene profile of the non-parenchymal cells used in the co-culture. As mentioned above, at least two non-parenchymal cell types (e.g., two fibroblast cell lines) are used in the methods of the invention. Typically one non-parenchymal cell type will promote a higher level of parenchymal cell (e.g., hepatocyte) functional activity.

Cellular proliferation can be measured by cell count and by routine examination under a microscope. Parenchymal cell growth is evident in histological sections through co-culture tissues. Such parenchymal cells can be identified as the largest cells of the co-culture and unlike stromal cells, which are irregularly-shaped and branched cells, are typically round. The parenchymal cells stain positively for tissue specific markers (e.g., in the liver such tissue specific proteins include albumin, fibrinogen, transferrin, and cytokeratin 19). The functional activity of the parenchymal cell will vary with the type of non-parenchymal cell. For example, the quantity and rate of expression of albumin by hepatocytes in co-culture will vary between the type of fibroblast cell line used in a co-culture.

Drug-induced liver disease represents a major economic challenge for the pharmaceutical industry since as many as 25% of drugs fail due to unforeseen human hepatotoxicity. Animal models provide a limited picture of human toxicity due to species variations as well as animal-to-animal variability, necessitating 5-10 animal experiments per experimental condition. Incorporation of in vitro liver models in the drug discovery/development process may provide several advantages: earlier elimination of potentially toxic drugs from the development pipeline, reduction in variability by allowing many hundreds of experiments per animal, and models of human liver tissue without patient exposure. However, current in vitro liver models typically lack long-term phenotypic hepatocyte (primary liver cells) stability and thus the chronic effects of xenobiotics and environmental toxins on liver function are not generally examined in vitro. Furthermore, although certain markers have been routinely used to assess liver function and health, such markers are somewhat limiting in the analysis of underlying long term effects such drug agents. Molecular analysis of markers identified and provided by the methods of the disclosure can be used to assess liver function, hepatocyte health and hepatocyte interaction with non-parenchymal cells (a necessary attribute for proper liver function).

Accordingly, in another aspect, the invention provides a method for screening drugs for dose limitations and cytotoxic liver effects by measuring polynucleotide and polypeptide expression of genes identified in the "functional profile" for the parenchymal cell being treated.

The invention also provides a method for screening a test agent for an affect on parenchymal cell function. The method includes contacting a parenchymal (e.g., liver) culture system with the agent and measuring expression of one or more genes in a functional profile for the parenchymal cell type being used. A wide variety of agents may be screened in the methods of the invention such as cytotoxic agents, growth/regulatory factors, pharmaceutical agents, and the like. For example, such agents can include polynucleotides, oligonucleotides, polypeptides, peptides, peptidomimetics, and small molecules. To this end, the co-cultures are maintained in vitro and exposed to the agent to be tested. The effect of a cytotoxic agent can be measured by its ability to modulate one or more genes in a function profile for the particular parenchymal cell type being cultured. Such gene expression changes can be measured using nucleic acid probes, PCR techniques, Northern blot, Southern blot, by measuring a polypeptide (e.g., by Western blot, and the like). Although, it will be recognized that the effect of such agents can be performed by measuring the effect on parenchymal cell activity, such measurements do not identify the underlying changes in co-culture gene expression necessary for proper tissue function.

Accordingly, a functional profile is obtained as described herein and the changes in the functional profile comprising molecular mediators measured before and after contact of the agent with a co-culture. Briefly, a first gene profile is obtained from co-culture of a parenchymal cell population and a first non-parenchymal cell population by measuring a tissue-specific function of the parenchymal cells and correlating the tissue-specific function with a gene expression profile of the first non-parenchymal cell population; and obtaining a second gene profile of a co-culture of the parenchymal cell population and a second non-parenchymal cell population by measuring the tissue-specific function of the parenchymal cells and correlating the tissue-specific function with a gene expression profile of the second non-parenchymal cell population. A functional profile is generated by identifying a change in the tissue-specific function and comparing the first and second gene expression profiles to identify one or more gene expression differences and correlating the one or more genes with the change in the tissue specific function, wherein the functional profile comprises the identity of candidate molecular mediators. A co-culture of a parenchymal cell population and the first and/or second non-parenchymal cell population is contacted with an agent to be tested under conditions such that the agent interacts with the cells, the co-culture is then assayed for a change in expression of one or more molecular mediators comprising the functional profile. A change in expression of such a molecular mediator is indicative of an agent that modulates tissue function. As described herein a change in the expression of molecular mediators can be performed using common molecular biology and/or protein assay techniques including, but not limited to, PCR, Northern/Southern/Western blots and the like.

In one aspect, the cytotoxicity to liver cells (e.g., human hepatocytes) of pharmaceuticals, anti-neoplastic agents, carcinogens, food additives, and other substances may be tested by utilizing the liver culture system of the invention and the functional profile for hepatocytes as identified in Tables 1 and 2.

For example, once a stable, growing liver co-culture is established the culture is exposed to varying concentrations of a test agent. After incubation with a test agent, the culture can be examined by phase microscopy to determine the highest tolerated dose—the concentration of test agent at which the earliest morphological abnormalities appear. Cytotoxicity testing can be performed using a variety of supravital dyes to assess cell viability in the culture, using techniques known to those skilled in the art. Molecular mediators listed in the functional profile, as identified in Tables 1 and 2, can be measured to determine the effect of the test agent on expression. The measurement of the genes and gene products can be performed by known techniques using, for example, PCR, and antibodies that specifically hybridize or interact with a gene or a gene product, respectively.

Similarly, the beneficial effects of drugs may be assessed using a co-culture; for example, growth factors, hormones, drugs which are suspected of enhancing hepatocyte formation or activity can be tested. In this case, stable cultures may be exposed to a test agent. After incubation, the cultures may be examined for viability, growth, morphology, cell typing, and the like as an indication of the efficacy of the test substance. In addition, the expression of the genes and gene products listed in a function profile obtained for the specific parenchymal cell (e.g., as identified in Tables 1 and 2) can be determined. Varying concentrations of the drug may be tested to derive a dose-response curve.

In another aspect, the disclosure provides a gene expression profiling system to study mechanisms of cell-cell interaction, and validate the role of candidate polypeptides and polynucleotides in culture models. The polynucleotide expression profile and the amount of polypeptide to be measure include those polynucleotides and polypeptides set forth in Tables 1 and 2. This may readily be assessed by vital staining techniques, ELISA assays, immunohistochemistry and the like. The effect of various drugs on normal cells cultured in the liver culture system may be assessed.

In addition to their use in drug discovery and development, molecules that upregulate and stabilize hepatocyte functions can be used to promote differentiation of stem cells (embryonic stem cells, adult progenitors) into hepatocytes for cell-based therapies. Conversion of stem cells into hepatocytes is an active area of research that can benefit from in vitro liver models in which hepatocytes dedifferentiate (decline of liver-specific functions) unless provided with the proper balance of non-parenchymal factors, extracellular matrix molecules and cell-cell contact.

Cell-based therapies for liver disease (e.g., bioartificial liver devices) currently rely on either primary hepatocytes or on cell-lines derived from primary hepatocytes or from hepatic carcinomas. In order for such therapies to gain widespread use and clinical effectiveness, liver cells have to be placed in a microenvironment that maintains or upregulates a crucial subset of their liver-specific functions. The administration of a compound or gene or gene product that upregulates or down regulates a gene identified in Table 1 and/or 2 can be used to improve such liver functions in bioartificial livers and in cultures systems.

Accordingly, the invention also provide methods and compositions to assist in in vitro maintenance of co-cultures of parenchymal cells (e.g., hepatocytes). For example, it is well established that hepatocytes rapidly lose liver-specific gene expression and functions (i.e. albumin secretion) in vitro unless their microenvironment is modified using extracellular matrix, media additives, or co-cultivation with non-parenchymal/stromal cells (e.g., fibroblasts). Modification of an in vitro microenvironment with the proper doses and combinations of molecular mediators identified using the methods of the invention can assist in the maintenance or upregulation of liver-specific functions of hepatocytes from a variety of species (rat, mouse, human, monkey, dog) commonly used in drug development. The disclosure demonstrates that liver-specific functions of rat, mouse and human hepatocytes are upregulated upon cocultivation with fibroblasts (and their secreted protein products) from which the candidate molecular mediators upregulated in hepatocyte and non-parenchymal cell interactions were identified.

TABLE 1

Figure 1A:
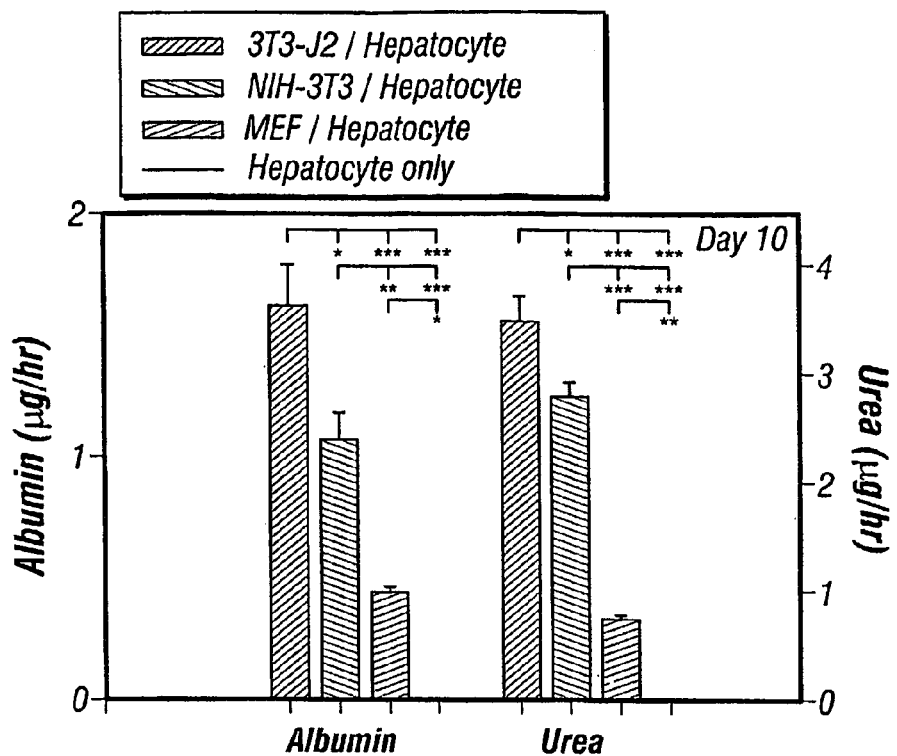
FIG. 1A-C shows the differential induction of liver-specific functions in rat hepatocytes upon co-cultivation with murine fibroblasts. A. Rate of albumin and urea production by hepatocytes on day 10 of co-culture with three different murine fibroblasts. B-C. In all co-cultures(B), hepatocytes exhibited polygonal morphology (arrow), distinct nuclei, and visible bile canaliculi, whereas hepatocyte morphology deteriorated in pure cultures (C). * $p<0.05$,  $p<0.01$, * $p<0.001$ (one-way ANOVA and Tukey's post-hoc test). Error bars represent standard error of the mean (n=4).

Fibroblast candidates genes whose expression profiles correlate positively with the inductive profile shown in FIG. 1A.

| Accession #* | Description |
|---|---|
| | Cell Surface |
| Z12171 | Delta-like 1 homolog (*Drosophila*) |
| NM_01010 | Endothelial differentiation, sphingolipid G-protein-coupled receptor, 3 |
| NM_007472 | Aquaporin 1 |
| BB776961 | T-cadherin (Cdh13) |
| BB053591 | vascular cadherin-2 |
| NM_011597.1 | tight junction protein 2 |

TABLE 1-continued

Fibroblast candidates genes whose expression profiles correlate positively with the inductive profile shown in FIG. 1A.

| Accession #* | Description |
|---|---|
| | Secreted |
| NM_010514 | Insulin-like growth factor II (IGF-II) |
| NM_010217 | Connective tissue growth factor |
| NM_008046 | Follistatin |
| NM_009263 | Secreted phosphoprotein 1 |
| X99572 | C-fos induced growth factor (VEGF-D) |
| U49513 | Small inducible cytokine A9 |
| U49430 | Ceruloplasmin |
| NM_009605.1 | Adiponectin (Acrp30) |
| NM_010217.1 | fibroblast inducible secreted protein |
| BI110565 | osteoblast specific factor 2 (fasciclin I-like) |
| M14951.1 | Mouse insulin-like growth factor II (IGF-II) |
| NM_009423.1 | Tnf receptor associated factor 4 (Traf4) |
| NM_007470.1 | apolipoprotein D |
| NM_017370.1 | Haptoglobin |
| NM_008046.1 | Follistatin |
| NM_031168.1 | Interleukin-6 |
| NM_010217.1 | Connective Tissue Growth Factor |
| NM_009141.1 | small inducible cytokine B subfamily, member 5 (Scyb5) |
| | Extracellular matrix or matrix remodeling |
| X53929 | Decorin |
| U69176.1 | laminin alpha 4 chain |
| | Transcription factors |
| NM_008416 | Jun-B oncogene |
| NM_007913 | Early growth response 1 |
| NM_008714 | Notch gene homolog 1 (*Drosophila*) |
| AV026617 | FBJ osteosarcoma oncogene |
| M21065 | Interferon regulatory factor 1 |
| M31419 | 204 interferon-activatable protein |
| | Other |
| X53824 | Splicing factor, arginine/serine-rich 3 |
| AB017020 | Heterogeneous nuclear ribonucleoprotein D-like protein JKTBP |
| L00993 | Autoantigen Ia (ss-b) |
| U00431 | High mobility group box 1 |
| Z72486 | DNA polymerase delta small subunit (pold2) |
| M86377 | Esk kinase |
| J00388 | Mouse dihydrofolate reductase gene: 3' end |
| X07967 | Pm1 protein |
| NM_007570 | B-cell translocation gene 2 |
| NM_009387 | Thymidine kinase 1 |
| NM_011369 | Shc SH2-domain binding protein 1 |
| NM_018734 | Guanylate nucleotide binding protein 4 |
| BB329808 | Interferon-induced protein 44 |
| BC027121 | Spindle pole body component 25 homolog (*S. Cerevisiae*) |
| BC004702 | Baculoviral IAP repeat-containing 5 |
| U80932 | Aurora kinase A |
| BB357585 | Solute carrier family 1 (glial high affinity glutamate transporter), member 3 |
| BB503935 | Leucine rich repeat containing 17 |
| AK019325 | Interferon, alpha-inducible protein |
| AI324988 | Minichromosome maintenance deficient 5, cell division cycle 46 (*S. Cerevisiae*) |
| BB533736 | Cysteine rich protein 61 |
| BB427399 | Apolipoprotein D |
| NM_010501 | Interferon-induced protein with tetratricopeptide repeats 3 |
| NM_008331 | Interferon-induced protein with tetratricopeptide repeats 1 |
| BQ033138 | 2'-5' oligoadenylate synthetase-like 2 |
| NM_021891.1 | fidgetin-like 1 |
| AW122347 (EST) | Rac gtpase-activating protein 1 |
| AA655369 (EST) | Translocase of inner mitochondrial membrane 8 homolog a, yeast |

Unknown function Accession #: AI037577, AI846197, AI841894, AI606951, AA940036, AI746846, AI551087, AA222883, AI848479, BM241237, AI853644, BC013672, BB820441
*The contents of each accession number is specifically incorporated herein by reference in its entirety. One of skill in the art can use the sequence information associated with each accession number to generate antibodies and/or nucleic acid primers and probes.

TABLE 2

Fibroblast candidates genes whose expression profiles correlate negatively with the hepatocyte functional profile shown in FIG. 1A.

| Accession #* | Description |
|---|---|
| | Cell Surface |
| L03529, AW046032 (EST) | Thrombin receptor (PAR-1) |
| X66084 | Hyaluronic acid receptor (CD44) |
| M90365 | Junction plakoglobin (cadherin associated) |
| M31131 | N-cadherin |
| M90364 | Beta-catenin |
| X59990 | Alpha-catenin 1 |
| AB006758 | BH-Protocadherin-a (Pcdh7) |
| AI854522 | Protocadherin-13 |
| Z17804 | Catenin src |
| AI852919 | Catenin (cadherin-associated protein), delta 2 (neural plakophilin-related arm-repeat protein) |
| NM_008377.1 | integral membrane glycoprotein |
| AF093620.1 | Stomatin |
| NM_009370.1 | transforming growth factor, beta receptor I (Tgfbr1) |
| B142324 | gap junction membrane channel protein alpha 1 |
| | Secreted |
| NM_011581.1 | thrombospondin 2 |
| NM_018857.1 | Mesothelin |
| AJ243964 | Dickkopf homolog 3 (*Xenopus laevis*) |
| X69619 | Inhibin beta-A |
| M70642 | FISP-12 protein |
| U77630 | Adrenomedullin |
| | Extracellular Matrix or Matrix Remodeling |
| X66976 | Procollagen, type VIII, alpha 1 |
| X62622, NM_011594.1 | Tissue inhibitor of metalloproteinase 2 |
| AI325305 | Matrix Metalloproteinase 14 |
| | Cytoskeletal associated |
| M12347 | Actin, alpha 1, skeletal muscle |
| U58513 | Rho-associated coiled-coil forming kinase 2 |
| U73199 | Rho interacting protein 2 |
| NM_010864 | Myosin Va |
| | Cell cycle |
| U09507 | Cyclin-dependent kinase inhibitor 1A (P21) |
| | Transcription factors |
| D76440 | Necdin |
| AJ002366 | General transcription factor IIH, polypeptide 1 |
| AI267126 | Kruppel-like factor 9 |
| U88064.1 | basonuclin |
| | Intracellular signaling |
| U15784 | Src homology 2 domain-containing transforming protein C1 |
| AF053367 | PDZ and LIM domain 1 (elfin) |
| U58883 | SH3 domain protein 5 |
| U58882 | LIM and SH3 protein 1 |
| | Other |
| X87817 | Dihydropyrimidinase-like 3 |
| Y13832 | Maternally expressed gene 3 |
| U41739, AI839950 (EST) | Four and a half LIM domains 1 |
| AW125478 (EST) | Protease, serine, 11 (Igf binding) |
| AI183109 (EST) | Translin-associated factor X |
| AJ007376 | DEAD box polypeptide, Y chromosome |
| NM_053191 | Protease inhibitor 15 |
| NM_007796 | Cytotoxic T lymphocyte-associated protein 2 alpha |
| NM_018857 | Mesothelin |
| D12713 | Sec23a (*s. Cerevisiae*) |
| AF441120.1 | Atrogin1 |
| NM_013623.1 | orosomucoid 3 |
| NM_007603.1 | Calpain 6 |
| M33324.1 | Mouse high molecular weight growth hormone receptor binding protein |

TABLE 2-continued

Fibroblast candidates genes whose expression profiles correlate negatively with the hepatocyte functional profile shown in FIG. 1A.

| Accession #* | Description |
| --- | --- |
| AB036749.1 | Porcupine D |
| M31775, AW046124 (EST) | Cytochrome b-245, alpha polypeptide |

Unknown function EST Accession #: AI848471, AI183109, AI648831

*The contents of each accession number is specifically incorporated herein by reference in its entirety. One of skill in the art can use the sequence information associated with each accession number to generate antibodies and/or nucleic acid primers and probes.

The functional profiles obtained by the methods of the invention define a set of molecular mediators that play a role in parenchymal cell growth, differentiation, and activity. These molecular mediators can also play a role in the differentiation and maintenance of stem cells (e.g., tissue progenitors including omnipotent and pluripotent progenitors). Furthermore, functional profiles of stem cells can be obtained using the methods of the invention. In this aspect, the parenchymal cells are replaced by stem cells and the process is performed as described herein.

Most stem cells require a 'feeder layer' for proper maintenance and culture (see, e.g., U.S. Pat. No. 6,090,622, the disclosure of which is incorporated herein by reference). For example, embryonic germ cells (EGs) or embryonic stem cells (ESs) and certain EC (embryonal carcinoma) cell lines will only retain the stem cell phenotype in vitro when cultured on a feeder layer of fibroblasts (such as murine STO cells, e.g., Martin, G. R. and Evans, M. J. Proc. Natl. Acad. Sci. USA 72: 1441-1445, 1975). In the absence of feeder cells or conditioned medium, ES or EGs spontaneously differentiate into a wide variety of cell types, resembling those found during embryogenesis and in the adult animal. With the appropriate combinations of factors, ES and EGs have been shown to generate cells of the hematopoietic lineage in vitro (Keller, G., et al., Mol. Cell. Biol. 13: 473-486, 1993; Palacios, R., E. Golunski, and J. Samaridis, Proc. Natl. Acad. Sci. USA 92: 7530-7534, 1995; Rich, T., Blood 86: 463-472, 1995), neurons (Bain, G., et al., Developmental Biology 168: 342-357, 1995; Fraichard, A., et al., J. Cell Science 108: 3161-3188, 1995), cardiomyocytes (heart muscle cells) (Klug, M., M. Soonpaa, and L. Field, Am. J. Physiol. 269: H1913-H1921, 1995), skeletal muscle cells (Rohwedel, J., et al., Dev. Biol. 164: 87-101, 1994), and vascular cells (Wang, R., R. Clark and V. Bautch, Development 114: 303-316, 1992). The factors responsible for maintaining the pluripotency of ES and EGs remain poorly characterized and are often dependent upon the species from which the cells have been harvested. The methods of the invention allow for the identification and characterization of these factors.

The invention provides functional profiles of various parenchymal cells that can be used to assist in the differentiation of stem cells along a particular lineage. For example, a functional profile of a hepatocyte parenchymal cell will identify a number of molecular mediators that play a role in the cell's function, maintenance and growth. Using the information of the functional profile, stem cells can be induced to differentiate along a hepatocyte lineage using molecular mediators identified in the functional profile. Similarly, functional profiles from other parenchymal cell types can be used to differentiate a stem cell along a desired lineage.

In yet another aspect, the functional profile obtained from the culture of stem cells on two different feeder layers (i.e., one that maintains and undifferentiated state and one that induces differentiation) can be used to identify molecular mediators that promote the maintenance of stem cells in an undifferentiated state.

There are a number of pluripotent stem cells known in the art. Thus, the term stem cell refers to a cell type that is not fully differentiated. In some instances the stem cell may be partially differentiated along a particular cell lineage, yet in other aspects the stem cell my be pluripotent or omnipotent in that it can differentiate into a number of different cell types.

There is a need for molecules which not only minimize liver damage/apoptosis, but, when provided in the appropriate combinations and doses, can promote growth and maintenance of liver cells, differentiation of stem cells in the liver (i.e., oval cells), up-regulate hepatocyte functions, and cause hepatocyte proliferation. In vitro liver models such as the one described herein can and have been used to discover such hepatoprotectants. The molecular mediators listed in Tables 1 and inhibitors that down regulate the mediators in Table 2 can serve as hepatoprotectants in vivo. As demonstrated herein, such molecular mediators of Table 1 can maintain viability and stabilize functions of primary hepatocytes, which are the most abundant and functional cells of the liver, in vitro. Similar approaches have proven useful in renal systems where molecules shown to stabilize renal epithelial cells in vitro have biological activity in vivo for promoting healing/regeneration of kidney.

Accordingly, in yet another aspect, a method of treating a subject having or at risk of having hepatic cell damage and/or a liver disease or disorder is provided. The method includes administering an agent that modulates the expression or activity of a gene or administering a gene or gene product identified by the accession numbers in Table 1 and/or 2. For example, the method includes administering to a subject in need of treatment a polypeptide or polynucleotide identified by the accession number in Table 1 or a polypeptide or polynucleotide that inhibits expression of a polynucleotide or its product identified in Table 2.

A therapeutically effective amount of an agent, polynucleotide or polypeptide above and a pharmaceutically acceptable carrier substance together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject in need of the compound. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. Continuous administration can also be obtained using an implantable or external pump to administer the therapeutic composition.

The dose of a peptide or therapeutic composition of the invention for treating a liver disease or disorder varies depending upon the manner of administration, the age and the body weight of the subject, and the condition of the subject to be treated, and ultimately will be decided by the attending physician or veterinarian. Such an amount of the agent or therapeutic composition as determined by the attending physician or veterinarian is referred to herein as a "therapeutically effective amount."

Also provided is a database comprising a functional profile for a parenchymal tissue. In one aspect the database is on computer readable medium such that a computer can locate and process the database. In another aspect, the database comprises Table 1 and/or Table 2 on a computer readable medium.

By "gene" is meant a polynucleotide comprising a sequence in the genome of the animal or cell that is linked at the 5' and 3' end to naturally occurring upstream and downstream sequences in the animal or cell. A gene includes a segment of DNA involved in producing a polypeptide chain; it may include regions preceding and following the coding region (leader and trailer) as well as intervening sequences (introns) between individual coding segments (exons). In some aspects, the accession numbers identified herein comprise a gene sequence for the referenced molecule; in other aspects, the accession number comprises a polynucleotide sequence lacking the intron(s), upstream and/or downstream non-coding regions. A "polynucleotide" refers to a polymeric form of nucleotides. In some instances a polynucleotide refers to a polymer of nucleotides that are not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or mRNA) independent of other sequences. The nucleotides can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

The term "isolated" as used in association with a polynucleotide means altered "by the hand of man" from its natural state; i.e., if it occurs in nature, it has been changed or removed from its original environment, or both. For example, a naturally occurring polynucleotide naturally present in a living animal, a biological sample or an environmental sample in its natural state is not "isolated", but the same polynucleotide separated from the coexisting materials of its natural state is "isolated", as the term is employed herein. Polynucleotides, when introduced into host cells in culture or in whole organisms, still would be isolated, as the term is used herein, because they would not be in their naturally occurring form or environment. Similarly, the polynucleotides may occur in a composition, such as a media formulation (solutions for introduction of polynucleotides, for example, into cells or compositions or solutions for chemical or enzymatic reactions). The terms "isolated" does not necessarily mean 100% isolated from other materials, but rather means that some substantial degree of isolation has taken place. For example, a substantially isolated polynucleotide includes polynucleotides that are 20% or more free of material with which it naturally associated. Isolated polynucleotide (or oligonucleotide) fragments can be manipulated using techniques in molecular biology to serve as probes and primers for hybridizing to genes or polynucleotides identified in Table 1 and/or 2, or in other functional profiles identified using the methods of the invention.

A polypeptide comprises at least two but typically 10 or more amino acids linked by amide bonds. A polypeptide includes any amino acid sequence and include modified sequences such as glycoproteins.

The working examples are provided to illustrate, not limit, the invention. Various parameters of the scientific methods employed in these examples are described in detail below and provide guidance for practicing the invention in general.

EXAMPLES

Hepatocytes were isolated from 2- to 3-month-old adult female Lewis rats (Charles River Laboratories, Wilmington, Mass.) weighing 180-200 g, by a modified procedure of Seglen. Detailed procedures for hepatocyte isolation and purification are known. Routinely, 200-300 million cells were isolated with 85%-95% viability, as judged by trypan-blue exclusion. Non-parenchymal cells, as judged by their size (<10 μm diameter) and morphology (non-polygonal), were less than 1%. Hepatocyte culture medium consisted of Dulbecco's Modified Eagle's medium (DMEM) with high glucose, 10% (v/v) fetal bovine serum, 0.5 U/mL insulin, 7 ng/mL glucagon, 7.5 μg/mL hydrocortisone, and 1% (v/v) penicillin-streptomycin.

Fibroblast Culture

3T3-J2 fibroblasts were the gift of Howard Green (Harvard Medical School). Mouse Embryonic Fibroblasts (MEFs) were the gift of James Thomson (University of Wisconsin-Madison), and NIH-3T3 cells were purchased from the American Type Culture Collection. 3T3 fibroblast culture medium consisted of DMEM with high glucose, 10% bovine calf serum and 1% penicillin-streptomycin. MEF media consisted of 10% fetal bovine serum instead of calf serum and was supplemented with 1% (v/v) nonessential amino acids.

Hepatocyte-Fibroblast Co-culture

Six-well plates were coated by adsorption of 0.13 mg/mL collagen-I in water for 1 h at 37° C. Purification of collagen from rat-tail tendons is known. Briefly, rat-tail tendons were denatured in acetic acid, salt-precipitated, dialyzed against HCl, and sterilized with chloroform. Pure hepatic cultures and co-cultures on decorin utilized co-adsorption of 0.13 mg/mL collagen-I and different concentrations of bovine decorin (Sigma). Protein-coated culture dishes were seeded with 125,000 hepatocytes in 1 mL of hepatocyte medium. After 24 hours, 125,000 fibroblasts were added in 1 mL of fibroblast medium. For co-culture experiments involving three different cell types, fibroblasts were growth-arrested by incubation in mitomycin-C (Sigma) supplemented media (10 μg/mL) for 2 h at 37° C. Each of the fibroblast types was then added to hepatocyte cultures at 350,000 cells per mL of its respective medium. For all co-cultures, the medium was replaced to hepatocyte medium 24 hours after fibroblast seeding and subsequently replaced daily.

Analytical Assays

Spent media was stored at −20° C. Urea concentration was assayed using a colorimetric endpoint assay utilizing diacetylmonoxime with acid and heat (Stanbio Labs, Boerne, Tex.). Albumin content was measured using enzyme linked immunosorbent assays (ICN-Cappel) with horseradish peroxidase detection and o-phenylenediamine (Sigma) as a substrate.

Microscopy

Specimens were observed and recorded using a Nikon Diaphot microscope equipped with a SPOT digital camera (SPOT Diagnostic Equipment, Sterling Heights, Mich.), and MetaMorph Image Analysis System (Universal Imaging, Westchester, Pa.) for digital image acquisition.

Gene Expression Profiling

Fibroblast RNA Isolation and Microarray Hybridization

Pure fibroblast cultures were grown in duplicate on collagen-coated polystyrene in their respective media for 24 hours, after which the media was replaced with hepatocyte media to mimic co-culture conditions to the extent possible. After an additional 24 hours, fibroblast RNA was extracted at ~80% prefluency using TRIzol-LS (Gibco). Each one of the duplicate fibroblast RNA samples was labeled, hybridized to an Affymetrix MG-U74Av2 microarray, and scanned. Double-strand cDNA was synthesized using a T7-$(dt)_{24}$ primer (Oligo) and reverse transcription (Gibco) cDNA was then purified with phenol/chloroform/isoamyl alcohol in Phase Lock Gels, extracted with ammonium acetate and precipitated using ethanol. Biotin-labeled cRNA was synthesized using the BioArray™ HighYield™ RNA Transcript Labeling Kit, purified over RNeasy columns (Qiagen), eluted and then fragmented. The quality of expression data was assessed using the manufacturer's instructions which included criteria such as low background values and 3'/5' actin and GAPDH (Glyceraldehyde-3-phosphate dehydrogenase) ratios below 2. The gene expression data was made available at "http:-//mtel.ucsd.edu/gene_expression/fibroblasts" as a community resource.

All expression data was scaled to a target intensity of 200 (Affymetrix MAS 4.0 software), which corresponds to ~3-5 transcripts per cell. Six microarray experiments were performed, which included 3 fibroblast cell lines prepared and hybridized in duplicate. These data were used to generate pair-wise comparison files for every cell type combination (i.e. 3T3-J2 replicate-1 versus NIH-3T3 replicate-1, 12 files total). These comparison files were then filtered using BullFrog filtering software to detect genes that were consistently differentially expressed. Criteria used for filtering were selected based on their ability to yield false-positive rates of less than 1% (# of genes differentially expressed in replicates/total genes). These criteria were set to be consistent in at least ten of twelve comparisons.

Microarray Data Analysis

Filtered data was exported to GeneSpring software (Silicon Genetics) and hierarchical clustering was employed with vector-angle distance metric to generate clusters of specific expression profiles. Other unsupervised (statistically driven) analysis methods (self-organizing maps and k-means clustering) yielded similar results to those obtained using hierarchical clustering. Clusters whose average expression profiles correlated with hepatocyte functional profiles (i.e., high-medium-low albumin and urea secretion) were selected as candidate genes for further analysis, which included functional annotation via the NetAffx analysis portal (Affymetrix), which integrates information from various public databases such as Genbank and Swissprot.

Western Blotting and Immunofluorescence

Fibroblasts grown on collagen-coated surfaces in hepatocyte medium were lysed in RIPA buffer (Upstate biotech) with protease inhibitor cocktail (Roche). Lysates were separated by polyacrylamide gel electrophoresis and transferred onto a PVDF membrane, blocked, incubated with primary antibody (Santa Cruz Biotech) and Horseradish peroxidase conjugated secondary antibody (Sigma), and visualized by chemiluminescence (Pierce SuperSignal). For indirect immunofluorescence, samples were fixed with paraformaldehyde, permeabilized with Triton-X100, stained with primary and Fluorescein isothiocyanate (FITC) conjugated secondary antibodies (Santa Cruz Biotech), and counterstained with Hoechst.

Statistical Analysis

Experiments were repeated 2-3 times with duplicate or triplicate samples for each condition. For functional assays, one representative outcome is presented where the same trends were observed in multiple trials. Statistical significance was determined using one-way ANOVA (analysis of variance) or Student's t-test and Tukey's post-hoc test on Prism (GraphPad, CA).

T-cadherin Fusion Protein Generation

Mouse T-cadherin cDNA was amplified by PCR (using mTcad in PBS as a template) with a forward primer set at the initiator codon and a FLAG-His6-tagged reverse primer set at 100 bp upstream from a unique Hind III site. The obtained PCR product was ligated into the pCEP4 mammalian vector (Invitrogen) and transfected into 293 cells with the Polyfect transfectant reagent according to the manufacturer's procedure (Qiagen). T-cadherin fusion protein expressing cells were selected and expanded in media containing 300 µg/ml Hygromycin. Serum free media supernatant was concentrated with an Amicon concentrator, cell debris removed by ultracentrifugation, fusion protein purified over a nickel column according to the manufacturer's protocol (Qiagen) and its purity checked by electrophoresis and silver staining (Daiichi Pure Chemicals Co.)

T-cadherin Fusion Protein Immobilization and Hepatocyte Culture

Tissue culture plates (polystyrene) were coated with 5% 3-aminopropyltrimethoxysilane (Sigma #26300) in 1 mM acetic acid for 10 min. After 2-3× washes in water, plates were incubated in 0.5% gluteraldehyde in PBS pH 7.4 for 30 min, followed by coating with 3-4 µg/ml NTA (nitrilotriacetic acid) ligand in PBS pH 7.9 (Qiagen #34491) for 20 min. A solution of 100 mM $NiSO_4$ was used to functionalize the plates with Nickel (20 min). Plates were subsequently treated with the fusion protein (1-50 µg/ml) in PBS (plus 1 mM Ca2+) pH 7.4 for 1-2 hours. Collagen-I (1 µg/mL in PBS) was then adsorbed to the T-cadherin coated surfaces for hepatocyte attachment. Hepatocyte-only and co-cultures were conducted as described in previous sections.

Gene Expression Profiling of Murine 3T3-J2 Fibroblasts after Interaction with Rat Hepatocytes in Co-culture Rat hepatocytes were plated at a density of 0.5 million cells per mL of hepatocyte culture medium per well of a 6-well plate that was pre-coated with type I collagen (0.1 mg/mL in water for 1 hr at 37° C.). After letting the hepatocytes attach and spread overnight, 0.5 million 3T3-J2 fibroblasts were seeded the next day in each well in fibroblast culture medium to create co-cultures. At day 4 of co-culture (with day 1 being fibroblast seeding) and then at day 9 (with fresh co-cultures), selective trypsinization was used to remove the fibroblasts. Briefly, the co-cultures were incubated in phosphate buffered saline for 5 minute to remove any residual traces of serum. Subsequently, these co-cultures were incubated with 0.25% Trypsin with EDTA for 3 minute to detach fibroblasts while leaving most of the hepatocytes attached to the substrate. The trypsin/fibroblast suspension was mixed with an equal amount of hepatocyte culture medium with serum and centrifuged at 1000 rpm for 5 minute. The supernatant was aspirated leaving the cell pellet at the bottom of the tube intact. This process was repeated two more times, after which Trizol Reagent (Invitrogen) was used (1 mL per million cells) to lyse and homogenize the fibroblast pellet. As controls, pure fibroblasts on collagen in hepatocyte medium were subjected to the identical protocol as that described for co-cultures above. RNeasy kit from Qiagen was used to purify total RNA, which was given to the Genechip Core at UC-San Diego for further processing and hybridization to Mouse 430 2.0 GeneChip whole genome arrays. The protocol used by the UCSD Core was similar to that reported in previous sections of this application.

The quality of gene expression data was assessed using the manufacturer's instructions which included criteria such as low background values and 3'/5' actin and GAPDH (Glyceraldehyde-3-phosphate dehydrogenase) ratios below 2. All microarray data was scaled to a target intensity of 2500 using GeneChip Operating Software (GCOS v1.2) to enable chip-to-chip comparisons. GCOS was further used to create comparison files for data from co-cultured J2s and pure ones (i.e. 3T3-J2 day 4 or 9 from co-culture versus 3T3-J2 day 4 or 9 from pure cultures). The data from the comparison files was exported to Microsoft Excel and filtered based on the following criteria: a call of 'increased' or 'decreased' for transcript levels in co-cultured versus pure J2s, a fold change of greater than 2, a call of 'present' in at least one of the two files being compared, and consistent change calls (i.e. increased) in both the day 4 and day 9 comparisons. Such filtering yielded 32 candidates (4 expressed sequence tags) which were upregulated in co-cultured J2s as compared to pure J2s, and 5 candidate genes which were down-regulated in co-cultured J2s as compared to pure ones. The genes being upregulated may directly or indirectly induce hepatic functions, while those being down-regulated may inhibit hepatocyte functions in co-culture.

CHO Cell Culture and Co-Culture

CHO-DG44 cells were transfected by calcium phosphate coprecipitation with pcD-Tcad (plasmid containing the coding region of T-cadherin) and pSV2neo (plasmid carrying neomycin resistance, American Type Tissue Culture, Rockville, Md.) as described previously (Vestal et al., J Cell Biol 119(2): 451-61, 1992, incorporated herein by reference). CHO cells are grown in MEM (Gibco Laboratories) containing 10% fetal calf serum, 1×HT supplement (Sigma Chemicals), L-glutamine, sodium pyruvate and non-essential amino acids. For co-culture studies, 750K CHO cells (either T-cad+ or null clones) were be seeded in CHO media (DMEM) on hepatocyte cultures. The media was changed to hepatocyte media the next day, and then replaced daily thereafter.

T-cad transfected CHOs were treated with 50 nM siRNA (siGENOME SMARTpool reagent M-049465, Dharmacon) targeted against the T-cadherin (also known as CDH 13) mRNA sequence (accession number NM_019707). siRNA was delivered via cationic liposome transfection reagent (Lipofectamine 2000, Invitrogen) according to manufacturer's protocol. Briefly, 100 pmol liposome reagent was diluted to 250 µl with 1×DMEM and incubated at room temperature for 15 min. 50 nM siRNA, also diluted to 250 µl with 1×DMEM, was then mixed with liposome dilution and incubated an additional 15 min.

Cells were incubated with the liposome-siRNA complexes in 1 mL total serum-free media. Six hours post-transfection, serum-free media was replaced with complete media. Eight to ninety-six hours post-transfection, protein was extracted from the fibroblasts, separated by SDS-PAGE, transferred to a PVDF membrane, incubated with primary antibody rabbit anti-T-cadherin, secondary antibody HRP-conjugated goat anti-rabbit IgG (Santa Cruz Biotechnology), visualized by chemiluminescence (Pierce SuperSignal), and quantified by densitometry.

siRNA T-cadherin Assay

T-cad transfected CHOs were treated with 50 nM siRNA (siGENOME SMARTpool reagent M-049465, Dharmacon) targeted against the T-cadherin (also known as CDH 13) mRNA sequence (accession number NM_019707, incorporated herein by reference). siRNA was delivered via cationic liposome transfection reagent (Lipofectamine 2000, Invitrogen) according to manufacturer's protocol. Briefly, 100 pmol liposome reagent was diluted to 250 µl with 1×DMEM and incubated at room temperature for 15 min. 50 nM siRNA, also diluted to 250 µl with 1×DMEM, was then mixed with liposome dilution and incubated an additional 15 min. Cells were incubated with the liposome-siRNA complexes in 1 mL total serum-free media. Six hours post-transfection, serum-free media was replaced with complete media. Eight to ninety-six hours post-transfection, protein was extracted from the fibroblasts, separated by SDS-PAGE, transferred to a PVDF membrane, incubated with primary antibody rabbit anti-T-cadherin, secondary antibody HRP-conjugated goat anti-rabbit IgG (Santa Cruz Biotechnology), visualized by chemiluminescence (Pierce SuperSignal), and quantified by densitometry.

Figures 1B, 1C:
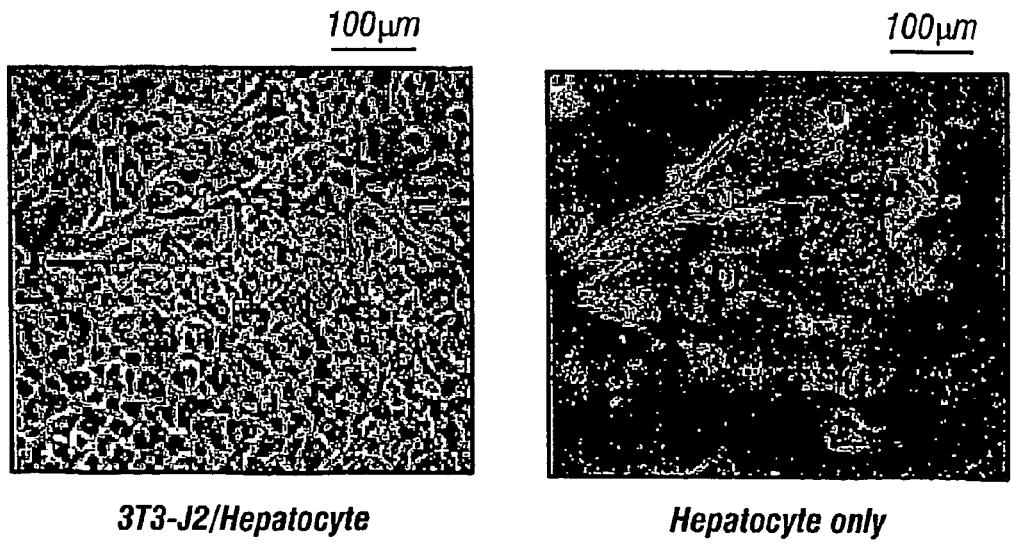

Differential Induction of Liver-specific Functions in Hepatocytes by Murine Fibroblasts In order to categorize non-parenchymal cells by their ability to induce hepatic functions, primary rat hepatocytes were co-cultured with three closely related murine fibroblasts: 3T3-J2 and NIH-3T3 cell lines, and primary mouse embryonic fibroblasts (MEFs). Induction of hepatic functions was scored by measurements of urea and albumin synthesis as markers of liver metabolic and synthetic function, respectively. FIG. 1A compares functions of hepatocytes in the three co-cultures to hepatocytes in pure culture. Hepatic functions were highest in the 3T3-J2 co-culture, followed by the NIH-3T3 co-culture, the MEF co-culture, and undetectable in hepatocytes cultivated alone. These trends were observed over many days. Inductive capacity of fibroblasts was therefore scored as follows: 3T3-J2>NIH-3T3>Mouse Embryonic Fibroblasts. Furthermore, hepatocyte morphology deteriorated in pure cultures (FIG. 1C) whereas all co-cultures were populated with polygonal hepatocytes with distinct nuclei and bright intercellular borders (FIG. 1B). Thus, 3T3-J2 cells were scored as 'high inducers', NIH-3T3 cells as 'medium inducers', and MEFs as 'low inducers' of hepatic functions.

Figure 2:
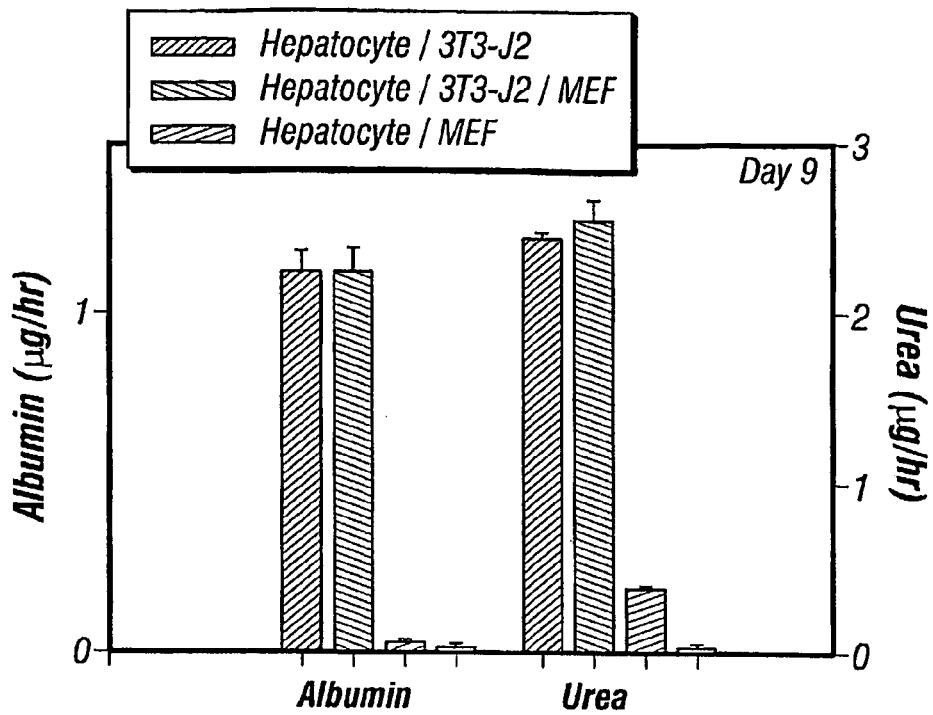
FIG. 2 shows the effect of poorly inductive mouse embryonic fibroblasts (MEFs) on hepatic functions in highly inductive 3T3-J2 co-cultures. These experiments were conducted to explore the potential for MEFs to actively inhibit highly functional co-cultures. Rate of albumin and urea production by hepatocytes on day 9 of co-culture with a mixture of mouse embryonic and 3T3-J2 fibroblasts.

In order to explore whether the poorly inductive fibroblasts (MEF) could inhibit hepatocyte function, hepatocytes were co-cultivated with a 1:1 mixture of highly inductive (3T3-J2) and poorly inductive fibroblasts (MEFs). Fibroblasts were growth-arrested with mitomycin C to prevent confounding effects of proliferation of both fibroblast populations. The results (FIG. 2) indicated that poorly inductive fibroblasts did not significantly diminish the function of hepatocytes in highly inductive cultures.

Gene Expression Profiling of Fibroblasts

Figure 3A:
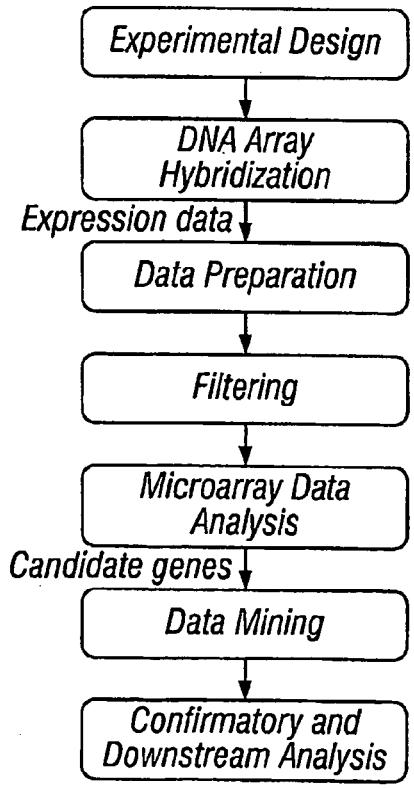
FIG. 3A-C shows gene expression profiling of fibroblasts. A. Flowchart depicting the use of DNA microarrays to obtain candidate genes involved with cell-cell interaction. Total RNA of fibroblasts (3T3-J2, NIH-3T3, Mouse Embryonic Fibroblasts) was harvested, labeled, and hybridized to Affymetrix GeneChips™. Expression data was normalized, filtered, analyzed and functionally annotated to obtain candidate genes. B. Phase contrast micrograph depicting fibroblast morphology (mouse embryonic fibroblasts) on collagen-coated polystyrene in hepatocyte medium. C. Clusterogram produced using hierarchical clustering with vector-angle distance metric is shown, where rows are gene expression values and columns represent different fibroblast cell types. Genes with similar expression profiles across conditions are clustered together. Average expression profiles of specific clusters that correlate positively and negatively with inductive profiles (shown as an inset) are shown to the right of the clusterogram.
Figure 3B:
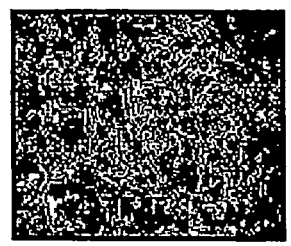
Figure 3C:
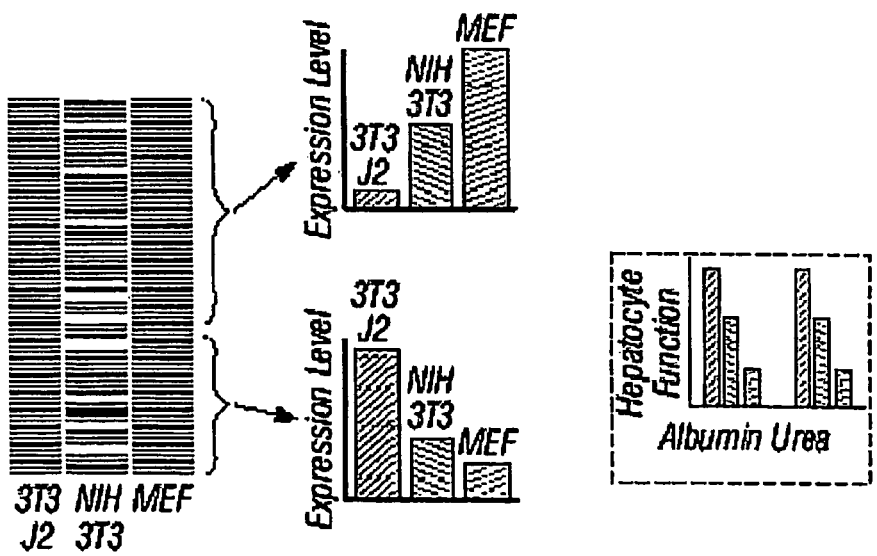

In order to investigate the potential mediators of epithelial-non-parenchymal interactions in hepatocyte co-cultures, gene expression profiling was used. As part of this process (FIG. 3A), Affymetrix GeneChips™ were used to first quantify messenger RNA levels in pure fibroblast cultures grown on type-I collagen in hepatocyte medium to mimic co-culture conditions to the extent possible (FIG. 3B). The data was then filtered to detect genes that were consistently differentially expressed across fibroblast cell lines. Subsequently, hierarchical clustering was employed (FIG. 3C) to obtain genes whose expression profiles correlated positively (high-medium-low) and negatively (low-medium-high) with the pattern of hepatocyte induction observed. In addition, all candidate genes were functionally annotated using the NetAffx analysis portal. In conducting further analysis, focus was made on proteins found on or around fibroblasts that may be involved with cell-cell communication including cell surface proteins, extracellular matrix, and secreted factors.

Cell Surface Proteins

Several studies have implicated cell surface proteins in epithelial-non-parenchymal interactions in hepatocyte co-cultures. The gene expression profiling yielded Dlk-1 (Delta-like homolog) whose expression profile correlated positively (i.e. high-medium-low) with ability of fibroblasts to induce functions in hepatocytes. Dlk-1 belongs to the EGF-like homeotic protein family that includes proteins such as the Notch receptor and its homologues. Dlk-1 is strongly expressed in the mouse fetal liver in hepatoblasts and has been implicated in differentiation of several non-hepatic cell types, suggesting it may play a functional role in hepatocyte co-cultures.

Further analysis of plakoglobin (γ-catenin) revealed that many of its interaction partners from the cadherin superfamily of cell adhesion molecules also had negative expression profiles (FIG. 4A). Classical cadherins, which are transmembrane proteins linked to the actin cytoskeleton via regulatory molecules such as catenins (FIG. 4B), may play roles in differentiation and heterotypic cell-cell interactions. In the liver, cadherins are expressed in both hepatocytes and surrounding nonparenchyma under both physiologic and pathophysiologic conditions. In co-cultures of hepatocytes with L-929 chaperone cells, E-cadherin expression correlated positively with induced hepatocyte functions; however, over-expression of E-cadherin in the developing liver prevents normal liver development. In co-cultures, protein expression was verified and localization of N-cadherin and β-catenin at homotypic and heterotypic junctions using immunofluorescence (FIG. 4C).

Extracellular Matrix

Matrix deposition and remodeling have been implicated as key features of hepatocyte co-cultures. The gene expression of collagen-VIII correlated negatively with inductive ability of fibroblasts. This non-fibrillar short-chain matrix protein is present in the arterioles and venules of normal liver and may play an instructional role in differentiation of other cell types. Even though the effect of collagen-VIII on hepatic functions has not been studied, other collagens (collagen-I) are responsible for dramatic changes in hepatocellular phenotype. Matrix remodeling via metalloproteinases and their inhibitors (tissue inhibitor of metalloproteinase; TIMP) may be an important feature of hepatocyte co-cultures. In the system described herein, the expression of TIMP-2 correlated negatively with inductive ability of fibroblasts, suggesting that an imbalance in matrix remodeling may also underlie the hepatic dysfunction found in MEF co-cultures.

A matrix protein whose expression profile correlated positively with fibroblast inductive ability was decorin, which is a chondroitin sulfate-dermatan sulfate proteoglycan that binds to collagen. Decorin is a major liver proteoglycan that shows early and strong upregulation during liver regeneration following partial hepatectomy. To validate the functional genomic approach, preliminary studies were conducted to investigate decorin's effect on hepatocellular functions in vitro. Due to the collagen-binding activity of decorin, hepatocyte function on collagen was compared to surfaces with co-adsorbed collagen and decorin. In pure hepatocyte cultures, albumin production was upregulated by 122% and urea secretion by 36% on decorin (FIG. 5A). In co-cultures of hepatocytes and MEFs ('low inducers'), hepatic functions were upregulated in a dose-dependent manner on adsorbed decorin as compared to collagen alone, resulting in up to 40% of albumin secretion rate seen in co-culture with 'high inducers' (FIG. 5B).

Secreted Factors

Studies assessing the role of soluble factors in hepatocyte co-culture models have yielded variable results. For example, treatment of hepatocytes with media 'conditioned' by non-parenchymal cells is typically ineffective. Nonetheless, secreted factors that are labile or are locally sequestered in matrix may play a role in cell-cell interaction. In the analysis herein, gene expression profile of vascular endothelial growth factor D (VEGF-D) correlated positively with induction of liver-specific functions. In addition to their role in angiogenesis, VEGFs play protective roles in liver regeneration (VEGF-A) and show dynamic pattern of expression in the developing liver (VEGF-D). Besides VEGF-D, Dickkopf homolog 3 exhibited a negative expression profile. Found primarily in mesenchymal lineages, Dickkopfs (dkk) are secreted proteins that have been implicated in modulating inductive epithelial-mesenchymal interactions.

As shown in FIG. 6, the rate of albumin and urea production by hepatocytes in co-culture with two different fibroblast cell types (3T3-J2 cells and MEF cells) is functionally different. The functional profile provided by comparison of the gene profiles of the two non-parenchymal cell lines indicates that the high hepatic function-inducing 3T3 J2 fibroblasts were positive for T-cadherin, where as low inducing Mouse Embryonic Fibroblasts (MEFs) were negative.

Mouse T-cadherin transfected CHO cells (T-cad CHOs) upregulate hepatocyte function in co-cultures over null wild-type co-cultures. For example, FIG. 7 shows a representative day, whereas similar trends were observed for multiple days over a 2-week experimental time course. Immunostaining of co-cultures showed that transfected CHOs retain T-cad protein expression in hepatic co-cultures. Additionally, hepatocytes were found to be negative for T-cadherin protein expression.

T-cad CHOs were treated with lipofectamine (control) or lipofectamine complexed with short interfering RNA (siRNA) specific for mouse T-cadherin (purchased from Dharmacon). Silencing of T-cad in CHOs persists from 24 hours up to 72 hours, as assayed by Western blotting (see FIG. 8). The upper band in each lane is the T-cad pre-processed peptide. T-cad CHOs treated with siRNA were subsequently co-cultured with rat hepatocytes. Such co-cultures showed a significant down-regulation of hepatocyte functions over mock-transfected (lipofectamine only) controls (see FIG. 9). FIG. 9 shows a representative day; a similar trend was seen in the long-term (e.g., 2 weeks). Over the experimental time course, there was a 36% decrease in total albumin production in siRNA treated CHO-hepatocyte co-cultures over controls.

When hepatocytes were plated on a substratum of co-adsorbed collagen (1 μg/ml) and purified histidine-tagged T-cadherin fusion protein at various concentrations. The concentrations of T-cadherin used did not influence hepatocyte attachment onto the substrate. Hepatocyte functions (albumin secretion, urea synthesis, and cytochrome P450 1A1 activity) varied in a dose-dependent manner with T-cadherin (see FIG. 10). CYP1A1 activity, which is a marker of liver's detoxification ability, was assayed via the de-alkylation of ethoxy-resorufin by CYP1A1 into the fluorescent resorufin.

Co-cultures of mouse embryonic fibroblasts (deficient in T-cadherin expression) and hepatocytes were created on co-adsorbed collagen (1 μg/ml) and purified T-cadherin protein (4 μg/ml). A functional upregulation was seen in T-cad cultures compared to collagen alone (see FIG. 11).

The foregoing experiments demonstrate that the use of the functional genomic approach of the invention to identify a functional profile is capable of identifying molecular mediators that play a role in parenchymal cell function. For example, the invention demonstrates that T-cadherin plays a role in hepatocyte function. The data demonstrate that CHO cell transfected with T-cadherin upregulated rat hepatocyte function in co-cultures over null wild-type control. Furthermore that knockdown of T-cadherin in transfected CHOs using RNA interference prior to initiation of co-cultures cause liver-specific functions to be down-regulated in the long-term (2 weeks). Culturing hepatocytes on co-adsorbed collagen and purified T-cadherin fusion protein upregulated liver specific function in a dose-dependent manner in pure cultures and co-cultures where non-parenchyma lacked endogenous T-cadherin expression.

A number of embodiments of the invention have been described. Nevertheless, it will be understood that various modifications may be made without departing from the spirit and scope of the invention. Accordingly, other embodiments are within the scope of the following claims.

What is claimed is:

1. A method of identifying candidate molecular mediators of parenchymal and nonparenchymal cell interactions, comprising:
    (a) obtaining a first co-culture of a parenchymal cell population and a first non-parenchymal cell population, measuring a tissue-specific function of the parenchymal cells and correlating the tissue-specific function with an inductive ability of the first non-parenchymal cell population;
    (b) obtaining a second co-culture of the parenchymal cell population and a second non-parenchymal cell population, measuring the tissue-specific function of the parenchymal cells and correlating the tissue-specific function with an inductive ability of the second non-parenchymal cell population;
    (c) identifying a change in the tissue-specific function resulting from co-culture of the parenchymal cell population with the first non-parenchymal cell population as compared to the second non-parenchymal cell population,
    wherein the non-parenchymal cell populations comprise fibroblast cells and wherein the parenchymal cell population comprises hepatocytes, and wherein the fibroblast cells are a cell line selected from the group consisting of 3T3-J2 fibroblasts, mouse embryonic fibroblasts, and NIH-3T3 fibroblasts, and
    wherein the functional profile comprises genes selected from the group consisting of Delta-like 1 homolog; Endothelial differentiation, sphingolipid G-protein-coupled receptor, 3; Aquaporin 1; T-cadherin (Cdh13); vascular cadherin-2; tight junction protein 2; Insulin-like growth factor II (IGF-II); Connective tissue growth factor; Follistatin: Secreted phosphoprotein 1; C-fos induced growth factor (VEGF-D); Small inducible cytokine A9; Ceruloplasmin: Adiponectin (Acrp30); fibroblast inducible secreted protein; osteoblast specific factor 2 (fasciclin I-like); Mouse insulin-like growth factor II (IGF-II); Tnf receptor associated factor 4 (Traf4); apolipoprotein D; Haptoglobin; Follistatin; Interleukin-6; Connective Tissue Growth Factor; small inducible cytokine B subfamily, member 5 (Scyb5); Decorin; laminin alpha 4 chain; Jun-B oncogene; Early growth response 1; Notch gene homolog 1 (Drosophila); FBJ osteosarcoma oncogene; Interferon regulatory factor 1; 204 interferon-activatable protein; Splicing factor, arginine/serine-rich 3; Heterogeneous nuclear ribonucleoprotein D-like protein JKTBP; Autoantigen la (ss-b); High mobility group box 1; DNA polymerase delta small subunit (pold2); Esk kinase; Mouse dihydrofolate reductase gene: 3' end; Pm 1 protein; B-cell translocation gene 2; Thymidine kinase 1; Shc SH2-domain binding protein 1; Guanylate nucleotide binding protein 4; Interferon-induced protein 44; Spindle pole body component 25 homolog; Baculoviral IAP repeat-containing 5; Aurora kinase A; Solute carrier family 1 (glial high affinity glutamate transporter), member 3; Leucine rich repeat containing 17; Interferon, alpha-inducible protein; Minichromosome maintenance deficient 5, cell division cycle 46; Cysteine rich protein 61; Apolipoprotein D; Interferon-induced protein with tetratricopeptide repeats 3; Interferon-induced protein with tetratricopeptide repeats 1; 2'-5' oligoadenylate synthetase-like 2; fidgetin-like 1; Rac gtpase-activating protein 1; and Translocase of inner mitochondrial membrane 8 homolog a.

2. The method of claim 1, wherein the tissue specific function is selected from the group consisting of: albumin production, fibrinogen production, TCDD-inducible CYP450 activity, and urea production.

3. A method for validating a molecular mediator of parenchymal and non-parenchymal cell interactions, comprising:
    (a) selecting a candidate molecular mediator identified by the method of claim 1, and (b) further testing the candidate molecular mediator for mediation of a parenchymal cell/non-parenchymal cell interaction in a co-culture of a parenchymal cell population and a non-parenchymal cell population;

wherein mediation of the parenchymal cell/non-parenchymal cell interaction validates the candidate molecular mediator as the molecular mediator of parenchymal and non-parenchymal cell interactions.

4. The method of claim 3, wherein the candidate molecular mediator selected is a cell surface molecule.

5. The method of claim 3, wherein the candidate molecular mediator selected is an extracellular matrix molecule.

6. The method of claim 3, wherein the candidate molecular mediator selected is a secreted factor.

7. The method of claim 3, wherein expression of the gene encoding the candidate molecular mediator correlates positively with the tissue-specific function.

8. The method of claim 3, wherein expression of the gene encoding the candidate molecular mediator correlates negatively with the tissue specific function.

9. A method of identifying candidate molecular mediators of parenchymal and nonparenchymal cell interactions, comprising:

(a) obtaining a first co-culture of a parenchymal cell population and a first non-parenchymal cell population, measuring a tissue-specific function of the parenchymal cells and correlating the tissue-specific function with an inductive ability of the first non-parenchymal cell population;

(b) obtaining a second co-culture of the parenchymal cell population and a second non-parenchymal cell population, measuring the tissue-specific function of the parenchymal cells and correlating the tissue-specific function with an inductive ability of the second non-parenchymal cell population;

(c) obtaining a third co-culture of the parenchymal cell population and a third non-parenchymal cell population, measuring the tissue-specific function of the parenchymal cells and correlating the tissue-specific function with an inductive ability of the third non-parenchymal cell population;

(d) identifying changes in the tissue-specific function resulting from co-culture of the parenchymal cell population with the first, second and third non-parenchymal cell populations;

(e) generating a functional profile, comprising:
  (i) identifying a first gene expression profile of a culture of the first non-parenchymal cell population, a second gene expression profile of a culture of the second non-parenchymal cell population, and a third gene expression profile of a culture of the third non-parenchymal cell population;
  (ii) comparing the first, second, and third gene expression profiles to identify a plurality of genes differentially expressed when comparing the profiles; and
  (iii) correlating the differential expression of the plurality of genes with the changes in the tissue-specific function;

wherein the functional profile comprises the plurality of genes differentially expressed and identifies the genes as candidate molecular mediators, wherein the non-parenchymal cell populations comprise fibroblast cells and wherein the parenchymal cell population comprises hepatocytes, and wherein the fibroblast cells are a cell line selected from the group consisting of 3T3-J2 fibroblasts, mouse embryonic fibroblasts, and NIH-3T3 fibroblasts, and wherein the functional profile comprises genes selected from the group consisting of Delta-like 1 homolog; Endothelial differentiation, sphingolipid G-protein-coupled receptor, 3; Aquaporin 1; T-cadherin (Cdh13); vascular cadherin-2; tight junction protein2; Insulin-like growth factor II (IGF-II); Connective tissue growth factor; Follistatin: Secreted phosphoprotein 1; C-fos induced growth factor (VEGF-D); Small inducible cytokine A9; Ceruloplasmin: Adiponectin (Acrp30); fibroblast inducible secreted protein; osteoblast specific factor 2 (fasciclin I-like); Mouse insulin-like growth factor II (IGF-II); Tnf receptor associated factor 4 (Traf4); apolipoprotein D; Haptoglobin; Follistatin; Interleukin-6; Connective Tissue Growth Factor; small inducible cytokine B subfamily, member 5(Scyb5); Decorin; laminin alpha 4 chain; Jun-B oncogene; Early growth response 1; Notch gene homolog 1 (Drosophila); FBJ osteosarcoma oncogene; Interferon regulatory factor 1; 204 interferon-activatable protein; Splicing factor, arginine/serine-rich 3; Heterogeneous nuclear ribonucleoprotein D-like protein JKTBP; Autoantigen la (ss-b); High mobility group box 1; DNA polymerase delta small subunit (pold2); Esk kinase; Mouse dihydrofolate reductase gene: 3' end; Pm 1 protein; B-cell translocation gene 2; Thymidine kinase 1; Shc SH2-domain binding protein 1; Guanylate nucleotide binding protein 4; Interferon-induced protein 44; Spindle pole body component 25 homolog; Baculoviral IAP repeat-containing 5; Aurora kinase A; Solute carrier family 1 (glial high affinity glutamate transporter), member 3; Leucine rich repeat containing 17; Interferon, alpha-inducible protein; Minichromosome maintenance deficient 5, cell division cycle 46; Cysteine rich protein 61; Apolipoprotein D; Interferon-induced protein with tetratricopeptide repeats 3; Interferon-induced protein with tetratricopeptide repeats 1; 2'-5' oligoadenylate synthetase-like 2; fidgetin-like 1; Rac gtpase-activating protein 1; and Translocase of inner mitochondrial membrane 8 homolog a.

* * * * *

UNITED STATES PATENT AND TRADEMARK OFFICE
CERTIFICATE OF CORRECTION

| | | |
|---|---|---|
| PATENT NO. | : 8,617,815 B2 | Page 1 of 1 |
| APPLICATION NO. | : 11/658980 | |
| DATED | : December 31, 2013 | |
| INVENTOR(S) | : Salman R. Khetani et al. | |

It is certified that error appears in the above-identified patent and that said Letters Patent is hereby corrected as shown below:

In the Claims

Column 30, line 15, in Claim 1, please insert:

--(d) generating a functional profile, comprising:
    (i) identifying a first gene expression profile of a culture of the first non-parenchymal cell population and a second gene expression profile of a culture of the second non-parenchymal cell population;
    (ii) comparing the first and second gene expression profiles to identify a plurality of genes differentially expressed when comparing the profiles; and
    (iii) correlating the differential expression of the plurality of genes with the changes in the tissue- specific function;
wherein the functional profile comprises the plurality of genes differentially expressed and identifies the genes as candidate molecular mediators,--

Signed and Sealed this
Seventh Day of July, 2015

Michelle K. Lee
*Director of the United States Patent and Trademark Office*

UNITED STATES PATENT AND TRADEMARK OFFICE
CERTIFICATE OF CORRECTION

PATENT NO. : 8,617,815 B2  Page 1 of 1
APPLICATION NO. : 11/658980
DATED : December 31, 2013
INVENTOR(S) : Khetani et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 777 days.

Signed and Sealed this
Twenty-second Day of September, 2015

Michelle K. Lee
*Director of the United States Patent and Trademark Office*